(12) United States Patent
Huang et al.

(10) Patent No.: US 12,007,388 B2
(45) Date of Patent: Jun. 11, 2024

(54) SYSTEM FOR SINGLE-MOLECULE ISOLATION FOR CELL POPULATIONS AND SINGLE CELLS, AND METHODS AND USES THEREOF

(71) Applicant: THE HONG KONG UNIVERSITY OF SCIENCE AND TECHNOLOGY, Kowloon (HK)

(72) Inventors: Pingbo Huang, Tseung Kwan O (HK); Qirui Zhao, Tseung Kwan O (HK)

(73) Assignee: The Hong Kong University of Science and Technology, Hong Kong (CN)

( * ) Notice: Subject to any disclaimer, the term of this patent is extended or adjusted under 35 U.S.C. 154(b) by 776 days.

(21) Appl. No.: 16/999,598

(22) Filed: Aug. 21, 2020

(65) Prior Publication Data
US 2021/0055290 A1   Feb. 25, 2021

Related U.S. Application Data

(60) Provisional application No. 62/922,657, filed on Aug. 22, 2019.

(51) Int. Cl.
| | |
|---|---|
| *G01N 33/543* | (2006.01) |
| *G01N 21/64* | (2006.01) |
| *G01N 27/74* | (2006.01) |
| *G01N 33/553* | (2006.01) |
| *G01N 33/58* | (2006.01) |

(52) U.S. Cl.
CPC ... *G01N 33/54333* (2013.01); *G01N 21/6458* (2013.01); *G01N 27/745* (2013.01); *G01N 33/553* (2013.01); *G01N 33/582* (2013.01)

(58) Field of Classification Search
CPC ......... G01N 33/54333; G01N 21/6458; G01N 27/745; G01N 33/553; G01N 33/582; G01N 33/54326; C12Q 1/6809; C12Q 1/6813; C12N 15/1013; B01L 3/5085; B01L 2300/0819; B01L 2300/0829
USPC ......... 422/407, 552; 435/6.1, 6.11, 7.2, 7.5, 435/288.4; 436/512, 523, 526, 534, 809; 977/789, 792, 793
See application file for complete search history.

(56) References Cited

U.S. PATENT DOCUMENTS

| | | |
|---|---|---|
| 4,376,110 A | 3/1983 | David et al. |
| 4,946,778 A | 8/1990 | Ladner et al. |

(Continued)

FOREIGN PATENT DOCUMENTS

| | | | | |
|---|---|---|---|---|
| WO | WO-2017095917 A1 * | 6/2017 | ........ | B01L 3/502761 |
| WO | WO 2018/140719 A1 | 8/2018 | | |
| WO | WO-2018140719 A1 * | 8/2018 | ......... | G01N 33/5304 |

OTHER PUBLICATIONS

Aggarwal, V., et al., "Single-molecule fluorescence microscopy of native macromolecular complexes," Current Opinion in Structural Biology (2016), 41:225-232.

(Continued)

*Primary Examiner* — Christopher L Chin
(74) *Attorney, Agent, or Firm* — SALIWANCHIK, LLOYD & EISENSCHENK

(57) ABSTRACT

The invention relates to the systems and methods for isolating single cells, capturing selected prey biomolecules within said cells, and detecting said prey biomolecules using a sensitive assay method. Also described herein are functionalized substrates and compositions for enabling the low limit of detection of selected prey biomolecules of selected cells.

27 Claims, 10 Drawing Sheets

(56) References Cited

U.S. PATENT DOCUMENTS 6,280,618 B2 8/2001 Watkins et al.
6,773,812 B2 8/2004 Chandler et al.

OTHER PUBLICATIONS

Jain, A., et al., "Probing cellular protein complexes using single-molecule pull-down," Nature (2011), 473:484-488.

Jain, A., et al., "Single molecule pull-down for studying protein interactions," Nature Protocols (2012), 7(3):445-452.

Wang, X., et al., "Toward Single-Cell Single-Molecule Pull-Down," Biophysical Journal (2018), 115:283-288.

Ryu, J.Y., et al., "Profiling protein-protein interactions of single cancer cells with in situ lysis and co-immunoprecipitation," Lab Chip (2019), 19:1922-1928.

Schulte, R. et al., "Single Bead Affinity Detection (SINBAD) for the Analysis of Protein-Protein Interactions," PLoS One (2008), 3(4):1-6:e2061. doi: 10.1371/journal.pone.0002061.

Kang, C-C., et al., "Single-Cell Western Blotting after Whole-Cell Imaging to Assess Cancer Chemotherapeutic Response," Analytical Chemistry (2014), 86:10429-10436.

Kozbor, D., et al., "The production of monoclonal antibodies from human lymphocytes," Immunology Today (1983), 4(3):72-79.

Waldo, G., et al., "Rapid protein-folding assay using green fluorescent protein," Nature Biology (1999), 17:691-695.

Bird, R. et al., "Single-Chain Antigen-Binding Proteins," Science (1988), 242:423-426.

Cote, R.J., et al., "Generation of human monoclonal antibodies reactive with cellular antigens," Proc. Natl. Acad. Sci. USA (1983), 80:2026-2030.

Huston, J.S., et al., "Protein engineering of antibody binding sites: Recovery of specific activity in an anti-digoxin single-chain Fv analogue produced in *Escherichia coli*," Proc. Natl. Acad. Sci. USA (1988), 85:5879-5883.

Huang, L., et al., "Centrifugation-Assisted Single-Cell Trapping in a Truncated Cone-Shaped Microwell Array Chip for the Real-Time Observation of Cellular Apoptosis," Analytical Chemistry (2015), 87:12169-12176.

Dawe, G.S., et al., "Cell Migration from Baby to Mother," Cell Adhesion & Migration (2007), Jan-March, 1(1):19-27.

Stelzl, U., et al., "A Human Protein-Protein Interaction Network: A Resource for Annotating the Proteome," Cell (2005), 122:957-968.

Wedeking, T., et al., "Single Cell GFP-Trap Reveals Stoichiometry and Dynamics of Cytosolic Protein Complexes," ACS Nano Letters (2015), 15:3610-3615.

Willott, J. F., et al., "Modulation of Presbycusis: Current Status and Future Directions," Audiology & Neuro-Otology (2001), 6:231-249.

Huse, W.D., et al., "Generation of a Large Combinatorial Library of the Immunoglobulin Repertoire in Phage Lambda," Science (1989), 246(4935):1275-1281.

Köhler, G., et al., "Continuous cultures of fused cells secreting antibody of predefined specificity," Nature (1975), 256(5517): 495-497.

Ward, S.E., et al., "Binding activities of a repertoire of single immunoglobulin variable domains secreted from *Escherichia coli*," Nature (1989), 341:544-546.

\* cited by examiner

Figures 9a-9f
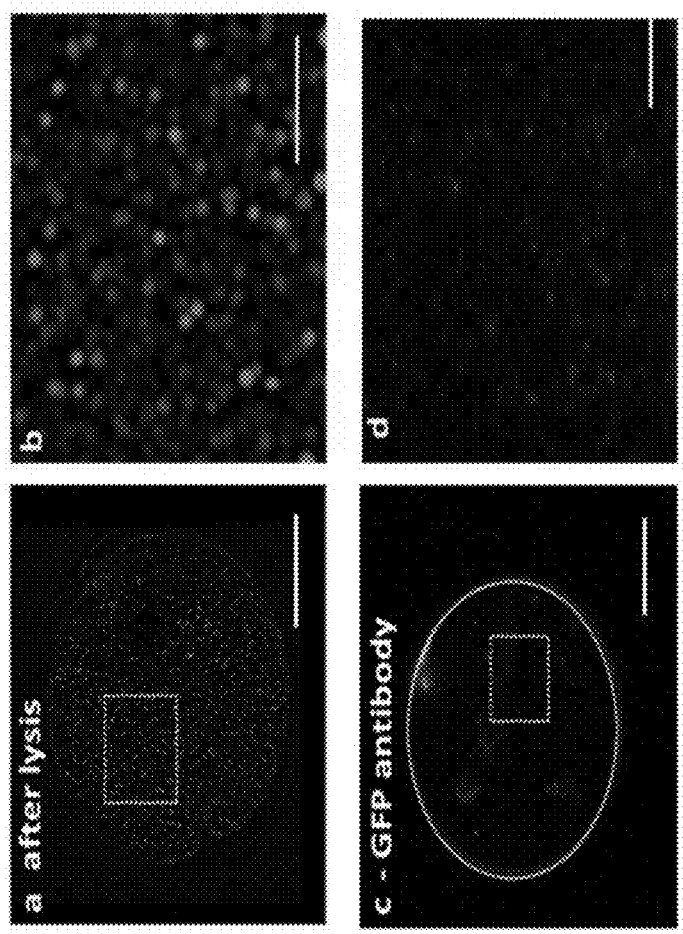
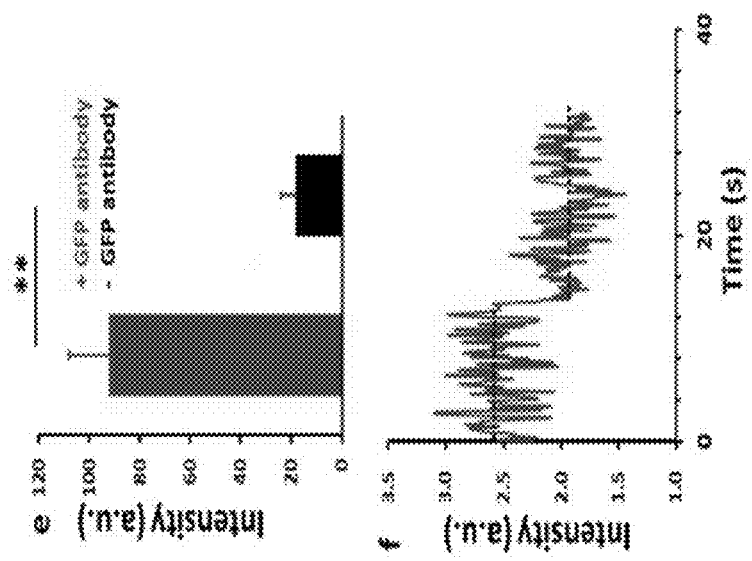

SYSTEM FOR SINGLE-MOLECULE ISOLATION FOR CELL POPULATIONS AND SINGLE CELLS, AND METHODS AND USES THEREOF

RELATED APPLICATIONS

This patent application claims the benefit in and to U.S. Provisional Application No. 62/922,657, filed on Aug. 22, 2019, the entire disclosure of which is incorporated herein by reference.

FIELD

The invention described herein relate generally to the field of protein and/or cell detection. Specifically, the embodiments described herein pertain to systems and methods for isolating single cells, capturing selected prey biomolecules within said cells, and detecting said prey biomolecules using a sensitive assay method.

INCORPORATION BY REFERENCE

All U.S. patents, U.S. patent application publications, foreign patents, foreign and PCT published applications, articles and other documents, references and publications noted herein, and all those listed as References Cited in any patent or patents that issue herefrom, are hereby incorporated by reference in their entirety. The information incorporated is as much a part of this application as if all the text and other content was repeated in this application, and will be treated as part of the text and content of this application as filed.

BACKGROUND

The following includes information that may be useful in understanding the invention. It is not an admission that any of the information, publications or documents specifically or implicitly referenced herein is prior art, or essential, to the presently described or claimed invention.

A protein never works alone: it works together with other proteins that function as its regulators, auxiliary subunits, or effectors. The functional associations of proteins typically require physical interactions with other proteins, or protein-protein interactions (PPIs), although they occasionally involve only soluble factors such as cAMP or $Ca^{2+}$. Therefore, PPIs are indispensable in nearly all aspects of diverse cellular processes, and identification of the interacting partners of a protein is essential for elucidating the protein's function and regulation.

For assessing PPIs in general, a commonly used and powerful technique is conventional co-immunoprecipitation (co-IP/pull-down) followed by western blotting. However, the conventional co-IP assay cannot be used for studying PPIs in rare cells such as sensory hair cells, circulating tumor cells, and embryonic stem cells: A single western-blotting assay typically requires ~$10^4$-$10^5$ cells and a single co-IP assay requires ~$10^5$-$10^6$ cells, and rare cells cannot be readily obtained in such large numbers (Schulte R., et al., "Single Bead Affinity Detection (SINBAD) for the Analysis of Protein-Protein Interactions," *PLoS ONE*, 3(4):e2061 (2008). https://doi.org/10.1371/journal.pone.0002061). For example, hair cells are extremely scarce; cochlear hair cells number ~3,300 per mouse cochlea and ~15,000 per human cochlea, and, furthermore, the efficiency with which these cells can be isolated from the surrounding supporting cells is extremely low (Willott J. F., et al., "Modulation of Presbycusis: Current Status and Future Directions," *Audiol Neurootol.*, 6:231-249 (2001)). Currently, PPIs in hair cells are investigated using only heterologous overexpression systems, but these are affected by artifacts and require substantiation through studies on endogenous proteins. This technical limitation of the conventional co-IP assay substantially hampers research on hair cells and on other rare cells and therefore calls for the development of single-cell pull-down techniques. Other methods for studying cell-to-cell variations include such as single-cell RNA-seq and single-cell western (Kang, C. C., et al., "Single-cell Western Blotting After Whole-Cell Imaging to Assess Cancer Chemotherapeutic Response," *Anal. Chem.*, 86(20):10429-10436 (2014)).

Recently, Jain et al. developed a single-molecule pull-down assay (SiMPull) combining the principles of conventional pull-down and single-molecule fluorescence microscopy (Jain, A., et al., "Single-molecule pull-down for studying protein interactions," *Nat. Protoc.*, 7(3):445-452 (2012)). SiMPull enables not only the evaluation of the stoichiometry of a protein complex, but also the examination of weak and transient PPIs featuring a $K_d$ in the micromolar range (Stelzl, U., et al., "A Human Protein-Protein Interaction Network: A Resource for Annotating the Proteome," *Cell*, 122(6):957-968 (2005)). These weak PPIs are readily disrupted in the multiple washing steps employed in conventional co-IP assays. However, SiMPull has not been widely used nor commercialized on a large scale since its development because the method presents a high technical barrier and is time-consuming.

Existing single-cell pull-down methods can isolate single cells but involve too many difficulties in expanding their use for cell-component analysis, as evidenced by the complete lack of any commercial system or method employing their use (Wedeking, T., et al., "Single Cell GFP-Trap Reveals Stoichiometry and Dynamics of Cytosolic Protein Complexes," *Nano Lett.*, 15(5):3610-3615 (2015); Wang, X., et al., "Toward Single-Cell Single-Molecule Pull-Down," *Biophysical Journal*, 115 (2): 283-288 (2018); Ryu, J. Y., et al., "Profiling Protein-Protein Interactions of Single Cancer Cells with in situ Lysis and Co-Immunoprecipitation," *Lab Chip.*, 19(11):1922-1928 (2019)). The applicability of these methods are problematic because (1) the methods can be used for analyzing slowly diffusing molecules only in bacteria or adherent-cell cultures but not primary- or suspension-culture cells (such as blood cells and circulating tumor cells); 2) the methods can only be used for analyzing a cell-surface protein with an antibody against its extracellular domain8; and (3) the technical barrier of the methods is astronomically high and therefore the methods cannot be used in common biological laboratories.

Thus, there remains a considerable unmet need for single-cell pull-down for cell component analysis.

SUMMARY

The invention described and claimed herein has many attributes and embodiments including, but not limited to, those set forth or described or referenced in this Summary. It is not intended to be all-inclusive and the invention described and claimed herein is not limited to or by the features or embodiments identified in this introduction, which is included for purposes of illustration only and not restriction.

This disclosure provides for the use of a substrate comprising a plurality of micron-sized features for the analysis of isolated single cells and/or selected components thereof. In some aspects, this disclosure provides for a system comprising a glass substrate comprising a plurality of micron-sized features, a plurality of antibody-coated beads, a plurality of primary antibodies against a bait biomolecule, a plurality of bait molecules, a plurality of target prey biomolecules, and a plurality of primary antibodies against said target prey biomolecule. The plurality of antibody-coated beads can comprise a plurality of secondary antibodies against the primary antibodies against the target bait biomolecules. The plurality of antibody-coated beads can comprise a plurality of primary antibodies against the target bait biomolecules. In some aspects, the plurality of antibody-coated beads can comprise a secondary antibody to the plurality of primary antibodies to a bait biomolecule.

In some aspects, the system can further comprise one or a plurality of types of cells. The cells can comprise one or a plurality of a type of target prey biomolecule. The plurality of antibody-coated beads can be located within the plurality of micron-sized features. The plurality of cells can be located in the plurality of micron-sized features. The plurality of cells can comprise cells having an average diameter of about 30 microns. The average diameter of the micron-sized features can be configured to selectively isolate cells having a diameter of less than the diameter of the micron-sized features.

In some aspects, the plurality of target prey biomolecules can comprise molecules which can be found in the cell membrane of said cells. In some aspects, the plurality of target prey biomolecules can comprise molecules which can be found in the cytoplasm of said cells. In some aspects, the bait biomolecules and prey biomolecules can be independently selected from: proteins, DNA, RNA, mRNA, tRNA, cRNA, antibodies, antibody fragments, ScFv's, peptides, and small molecules. The DNA or RNA can be further modified with biotin.

In some aspects, the system can further comprise a cell lysis buffer, which can comprise a non-denaturing detergent.

In some aspects, the plurality of micron-sized features can comprise a series of wells having round holes each of which has a mean average diameter between about 15 microns to about 45 microns, a mean average distance between the center of each hole ranging from about 100 microns to about 5000 microns, and a mean average depth of each hole of about 25 microns to about 150 microns. In some aspects, the diameter of the series of wells can be about 30 microns. The distance between the center of each hole can be about 150 microns. The depth of each hole can be about 75 microns. In some aspects, the plurality of cells can comprise cells having an average diameter of less than the diameter of the mean average round holes of the wells. In some aspects, the plurality of micron-sized features can be directly etched into the glass substrate. In some aspects, the plurality of micron-sized features can be formed from PDMS (polydimethylsiloxane). The substrate can comprise cured PDMS. The glass substrate can be a glass coverslip having a thickness of 0.085 mm to 0.64 mm. In some aspects, the glass substrate is configured to be measureable with TIRF (total internal reflectance specstroscopy). The round holes can be circle-shaped, ring-shaped, spherical-shaped or other shapes that resemble a circle. The holes in the series of wells can also be oval-shaped or squoval shaped. The wells can be flat bottomed (F-well), round bottomed (U-well), C-bottomed (which is a combination of flat and round bottoms, such as a flat-bottomed well with curved edges at the bottom) (C-well); star well (which is a well with modified C-shaped geometry with a one or a plurality of fins placed at the bottom and/or sides of the well); or V-bottomed (which is a conical-shaped well) (V well).

In some aspects, the plurality of antibody-coated beads further can comprise a magnetic bead, which itself can comprise an iron oxide core and a outerlayer comprising a functional group which enables the binding of a biomolecule, preferably a capture agent, preferably an antibody. In some aspects, the system can further comprise a magnet.

In some aspects, this disclosure provides a system comprising a glass substrate comprising a plurality of micron-sized features, a plurality of first capture agents to a bait biomolecule, a plurality of bait biomolecules, a plurality of a prey biomolecules, a plurality of second capture agents to said prey biomolecules, wherein the plurality of first capture agents to a bait molecule further can comprise a magnetic bead. The bait biomolecules, the prey biomolecules, or both can be linked to a fluorophore. The plurality of antibody-coated beads can be located within the plurality of micron-sized features. In some aspects, the system can further comprise one or a plurality of types of cells, and optionally the cells can comprise one or a plurality of a type of prey biomolecule. In some aspects, the system can further comprise a magnet. In some aspects, the plurality of cells can be in the plurality of micron-sized features. The plurality of micron-sized features can comprise a series of wells having round holes each of which has a mean average diameter between about 15 to about 45 microns, a mean average distance between the center of each hole ranging from about 100 to about 5000 microns, and a mean average depth of each hole of about 25 to about 150 microns.

This disclosure provides for a method for identifying a biomolecule-biomolecule interaction, comprising the steps: (a) contacting one or a plurality of cell types with a system of as described herein, (b) presenting a lysis buffer to the system, and (c) imaging the system by fluorescence microscopy. In some aspects, at least one of the system components can be fluorescently labeled. The fluorescene microscopy can be selected from TIRF or confocal microscopy.

This disclosure provides for a method for identifying a biomolecule-biomolecule interaction, the method comprising the steps: (a) contacting a substrate comprising a plurality of micron-sized features with one or a plurality of cell types, wherein a portion or all of the one or plurality of cell types enter a portion or all of the plurality of micron-sized features; (b) presenting a plurality of antibody-coated magnetic beads to said substrate, wherein the antibody-coated magnetic beads comprise an antibody to a bait biomolecule; (c) optionally, applying a magnetic field to said antibody-coated beads; (d) contacting said substrate with a lysis buffer; (e) forming a complex selected from the antibody of the antibody-coated magnetic beads and a bait biomolecule, the bait biomolecule and the prey biomolecule, or all of the antibody of the antibody-coated magnetic beads to the bait biomolecule to the prey biomolecule; (f) presenting an antibody or antibody complex to the prey biomolecule; (g) imaging the antibody or antibody complex to the prey biomolecule by fluorescence microscopy. In some aspects, the cells can comprise a bait biomolecule and/or a prey biomolecule. In some aspects, the antibody or antibody complex to the prey biomolecule can be fluorescently labelled. In some aspects, the antibody complex to the prey biomolecule can comprise a primary antibody to the prey biomolecule, and a secondary antibody to said primary antibody to the prey biomolecule, wherein the secondary antibody can be fluorescently labeled. In some aspects, the prey biomolecule and bait biomolecule can be independently selected from: proteins, DNA, RNA, mRNA, tRNA, cRNA, antibodies, antibody fragments, ScFv's, peptides, and small molecules.

In some aspects, the step of (g) imaging the antibody or antibody complex to the prey biomolecule by fluorescence microscopy, can be performed by TIRF (total internal reflectance spectroscopy) or confocal microscopy.

In some aspects, the methods described herein can have an analyte signal-to-noise of higher than 10, than 12, than 15, or 20.

In some aspects, the methods described herein can isolate one prey biomolecule per nanometer-sized functionalized bead.

BRIEF DESCRIPTION OF THE FIGURES

The accompanying drawings, which are incorporated herein and form a part of the specification, illustrate the aspects of the present disclosure and, together with the description, further serve to explain the principles of the aspects and to enable a person skilled in the pertinent art to make and use the aspects. The drawings are for illustration purposes only, show exemplary non-limiting embodiments, and are not necessarily drawn to scale.

FIG. 2a (noted as "a") shows GFP in pre-made lysate of GFP-expressing HEK293T cells was pulled down by streptavdin-coated magnetic nanobeads that were surfaced-modified with biotinylated 2nd antibody plus anti-GFP, anti-FLAG, or anti-HA antibody. In addition, the cell lysate of non-transfected HEK293T cells was used as negative control. The very high signal-to-noise (S/N) ratio suggest that GFP was specifically pulled down by anti-GFP antibody. Scale bars: 10 μm. FIG. 2b (noted as "b") shows the average intensity of fluorescent molecules per imaging area. Error bars denote standard deviation (s.d.) FIG. 2c (noted as "c") shows the distribution of the photobleaching step of GFP molecules in FIG. 2a. Most of fluorescent spots are single molecules.

FIG. 3a (noted as "a") shows a schematic of PKA complex and its activation by cAMP. R, regulatory subunit; C, catalytic subunit. FIG. 3b (noted as "b") shows upper images: Pull-down of PKA-C-eGFP (green) also pulled down PKA-R-mCherry (red). Lower images in FIGS. 3B and 3c (noted as "c"): corresponding surface plot maps of the upper images. FIG. 3c shows upper images: Pull-down of PKA-C-eGFP (green) did not pull down mCherry (red). All analyses were performed using confocal microscopy. Scale bars: 3 microns.

FIG. 5a (noted as "a") shows in the left panel microposts were fabricated on silicon wafers by standard soft lithography methods. The features were arranged in a square configuration containing 9 blocks of 10×10 micropillars (with diameter of 30 microns and height of 70 microns). Right panel; Magnification of the boxed. FIG. 5b (noted as "b") shows in the left panel; Corresponding features of panel a in PDMS gel. Right panel; Magnification of the boxed area. Scale bars: 1.5 mm in left panels; 400 microns in right panels FIG. 6a (noted as "a") shows cells trapped in microwells in the view field (pointed with white arrow). Scale bars, 100 μm. FIG. 6b (noted as "b") shows the summary data of cell numbers in each well in a chip (n=3). ~40% of total microwells are occupied by cells; ~85% of cell-occupied microwells are single cells, and this ratio would presumably increase with applying more diculted cells.

FIG. 7a (noted as "a") shows the top view of a microwell with a HEK293T cell only. FIG. 7b (noted as "b") shows the top view of a microwell with a HEK293T cell after applying magnetic nanobeads to the chip.

FIG. 8a (noted as "a") shows after a single cell was trapped by a microwell, surface-modified magnetic nanobeads (100±30 nm in diameter) were applied to the microwell chip. The nanobeads are streptAvidin-coated magnetic nanobeads modified with biotinylated 2nd antibody and 1st antibody of bait protein. FIG. 8b (noted as "b") shows that to lyse the cell in situ, the lysis buffer was added to the top of the chip. After cell lysis and protein capture, magnetic nanobeads were dragged to the microwell bottom by a magnet and imaged by TIRF or confocal microscopy.

FIGS. 9a-9f show GFP pull-down with a single cell in microwell. FIG. 9a (noted as "a") shows GFP pulled down by GFP-antibody-coated magnetic nanobeads after cell lysis. Most fluorescent spots were small but some were large. FIG. 9b (noted as "b") shows the Magnification of the boxed area in panel d. Small spots were indicated by arrowheads and large spots by arrows. FIG. 9c (noted as "c") shows GFP were not pulled down by without GFP-antibody-coated magnetic nanobeads after cell lysis in a negative control experiment. FIG. 9d (noted as "d") shows the magnification of the boxed area in FIG. 9c. FIG. 9e (noted as "e") shows a small GFP spot display one-step photobleaching in a photobleaching experiment suggesting the presence of a single GFP molecule in the spot. FIG. 9f (noted as "f") shows the total intensity of dots in FIGS. 9b and 9d Scale bars: panels FIGS. 9a and 9c: 20 microns; panels FIG. 9b and FIG. 9d: 3 microns.

FIG. 10a (noted as "a") show Anti-GFP coated magnetic nanobeads pulled down both PKA-C-eGFP (green) and PKA-R-mCherry (red) in a single cell in the absence of cAMP but, as shown in FIG. 10b (noted as "b"), pulled down only PKA-C-eGFP (green) in the presence of cAMP. FIG. 10c (noted as "c") show Anti-GFP coated magnetic nanobeads pulled down PKA-C-eGFP (green) and PKA-R-HA(red) in a single cell. PKA-R-HA was visualized by immunostaining with anti-HA antibody and Alexa-561-conjugated 2nd antibody. FIG. 10d (noted as "d") shows few HA positive spots were seen when PKA-R-HA was replaced by PKA-R-GFP, suggesting the HA staining in FIG. 10c was HA-specific. In FIGS. 10a-10d, lower images are the magnification of the small boxed area in the upper overlay images and right images are their corresponding surface plot maps; scale bars: upper-left, 20 microns; lower-left, 3 microns; right, 3 microns.

DETAILED DESCRIPTION

Figure 1:
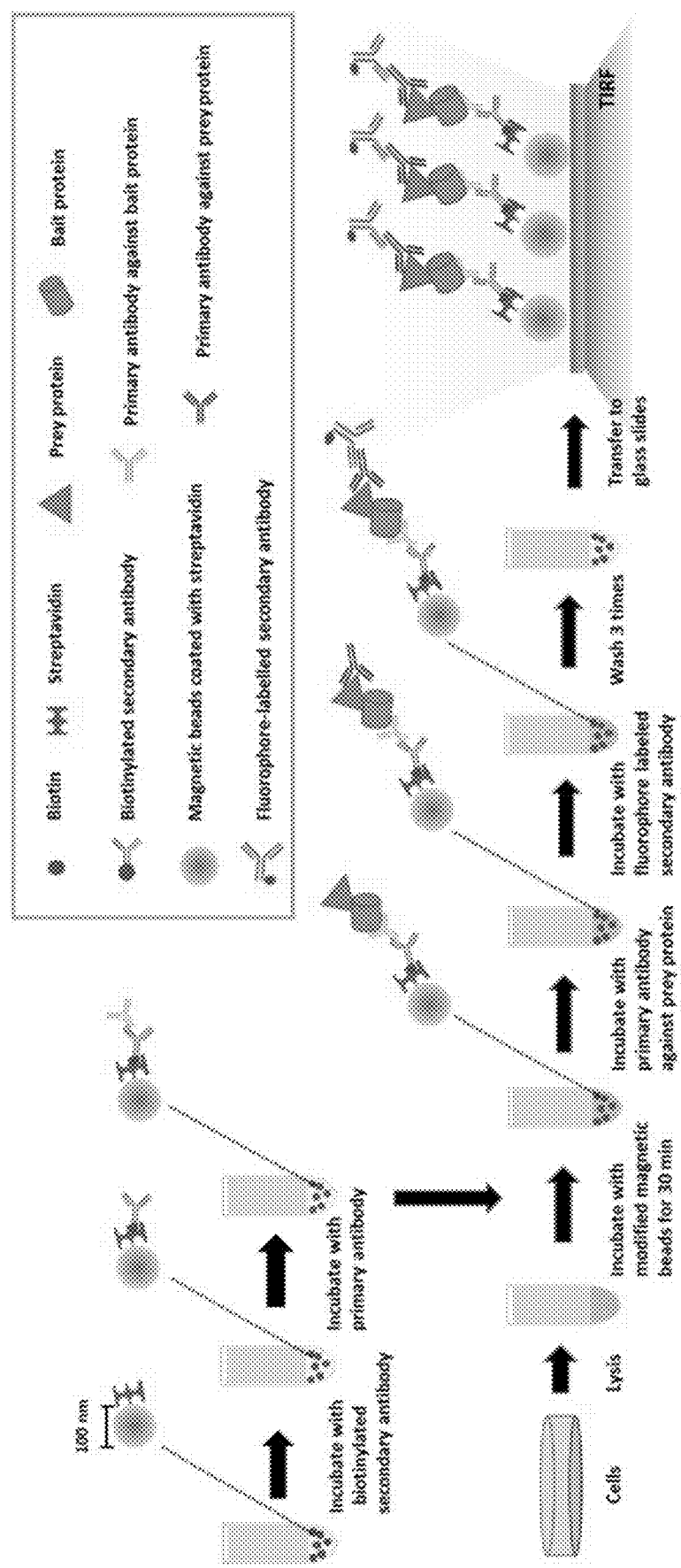
FIG. 1 shows a representative schematic of nanobead-based SiMPull for cell populations. Streptavidin-coated magnetic nanobeads are modified by immobilizing the primary antibody on their surface for capturing the target protein (bait protein) (see detailed protocol below). Cells are lysed and the magnetic nanobeads are added to the lysates and incubated for 30 min, and after the prey protein is captured by the beads, the protein is detected using a specific primary antibody and fluorescently labeled secondary antibodies. The nanobeads are washed thrice to remove non-specifically bound proteins, transferred to glass slides and covered with coverslips, and imaged using a TIRF microscope. In certain cases, the bait protein or the prey protein is fluorescently labeled and can be visualized directly.

This description of the exemplary embodiments is intended to be read in connection with the accompanying drawings, which are to be considered part of the entire written description. Additionally, the section headings used herein are for organizational purposes only, and are not to be construed as limiting the subject matter described.

It has also been discovered that a nanobead-based approach for single-cell isolation and analysis designed for cell populations and, more importantly, single cells, can be used by employing the systems described herein. The methods described herein are substantially simpler and faster than conventional pull-down methods and are also considerably more widely applicable to all cell types. These two crucial features enable the universal application of the methods described herein in common biological and clinical laboratories. The methods described herein, by providing for the application of single-cell isolation and analysis in a single-cell capture format described herein represents a major technical breakthrough for the field of single-cell research.

Conventional co-immunoprecipitation methods (co-IP/pull-down) commonly used for accessing protein-protein interactions (PPIs) require large numbers of cells and are thus unsuitable for studying PPIs in rare cells such as sensory hair cells, circulating tumor cells, and embryonic stem cells; this substantially hampers rare-cell research and therefore calls for the development of single-cell pull-down techniques. Equally important, such single-cell pull-down techniques can enable investigation of cell-to-cell variation in PPIs.

Described herein is a magnetic nanobead-based approach for SiMPull for cell populations and, more importantly, single cells, which utilizes a substrate comprising a plurality of micron-sized features.

The systems and methods described herein are useful for, inter alia:
1) Assessing the cell heterogeneity in complex tissue samples. For example, in one embodiment, the relative expression of EGFR and GRB2 can be measured in different cells using the methods and systems described herein.
2) Measuring the existence of, and degree of, complex cellular protein interactions and dynamic networks of signaling pathways. For example, in one embodiment, HIF repressor pathways and mTOR signaling pathways in the tumor microenvironment can be measured using the methods and systems described herein.
3) Exploring cell-to-cell variation in viral infections. For example, in one embodiment, influenza virus and COVID-19 virus populations and cellular infection rates contributed by virus and host factors using the methods and systems described herein.
4) Profiling cell type percentage in complex tissues. For example, in one embodiment, immune cell populations in the tumor microenvironment can be measured and quantified using the methods and systems described herein.
5) Validating protein information of single-cell RNA-seq data can be performed using the methods and systems described herein.
6) Detecting small molecules in blood (for example, hemoglobin cells) or lymphatic fluid can be performed using the methods and systems described herein.

Definitions

The term "comprising," which is synonymous with "including," "containing," or "characterized by," is inclusive or open-ended and does not exclude additional, unrecited elements or ingredients from the medicament (or steps, in the case of a method). The phrase "consisting of" excludes any element, step, or ingredient not specified in the medicament (or steps, in the case of a method). The phrase "consisting essentially of" refers to the specified materials and those that do not materially affect the basic and novel characteristics of the medicament (or steps, in the case of a method).

The term "tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The terms "cancer" and "cancerous," as used herein, refer to or describe the physiological condition in mammals that is typically characterized by unregulated cell growth and/or proliferation. Some cancers are composed of rapidly dividing cells while others are composed of cells that divide more slowly than normal. Types of cancer examples can include or exclude, for example, carcinoma, lymphoma (e.g., Hodgkin's and non-Hodgkin's lymphoma), blastoma, sarcoma, and leukemia. More particular examples of such cancers can include or exclude, for example, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "contacting" as used herein, refers generally to providing access of one component, reagent, analyte or sample to another. For example, contacting can involve mixing a solution comprising a functionalized nanoparticle with a sample comprising a cell. The solution comprising one component, reagent, analyte or sample may also comprise another component or reagent, such as dimethyl sulfoxide (DMSO) or a detergent, which facilitates mixing, interaction, uptake, or other physical or chemical phenomenon advantageous to the contact between components, reagents, analytes and/or samples, in some embodiments of the invention, contacting involves adding a solution comprising a functionalized nanoparticle to a sample comprising a cell utilizing a delivery apparatus, such as a pipette-based device or syringe-based device.

As used herein, the term "subject" or the like, including "individual," and "patient", all of which may be used interchangeably herein, refers to any mammal, including humans, domestic and farm animals, and zoo, wild animal park, sports, or pet animals, which can include or exclude dogs, horses, cats, sheep, pigs, cows, etc. The preferred mammal is a human, including adults, children, and the elderly. Preferred sports animals are horses and dogs. Preferred pet animals are dogs and cats. The subject may be, for example, an aquatic park animal, which can include or exclude a dolphin, whale, seal or walrus. In certain embodiments, the subject, individual or patient is a human.

As used herein, the term "sample" may refer to a solution, suspension, mixture, or undiluted amount of an aqueous solution comprising a cell of interest. In some embodiments, the cell of interest is a rare cell. In some embodiments, the rare cell is a skin cell. In some embodiments, the rare cell is a circulating cancer cell. In some embodiments, the aqueous solution further comprises buffers, stablizers, cell lysis agents, preservatives, EDTA, etc. In some embodiments, a "sample" is a bodily fluid. As used herein, the term "bodily fluid" may refer to any fluid that can be isolated from the body of a subject which can include or exclude: whole blood, plasma, serum, bile, saliva, urine, tears, perspiration, cerebrospinal fluid (CSF), semen, swabbed samples (e.g. cheek swabs, nasal swabs, throat swabs, etc.), mucus, sputum, menstrual blood, menstrual fluid, vaginal mucus, amniotic fluid, synovial fluid, breast milk, lochia, Rheum, lymph, pus, and the like. In some embodiments, bodily fluid may more particularly refer to whole blood, serum, urine, saliva, swabbed samples, mucus, or semen. In certain embodiments, bodily fluid may more particularly refer to whole blood, serum, urine, or saliva. In some embodiments, the bodily fluid may include an analyte of interest (e.g., a target prey biomolecule).

The terms "specifically binding" and "specific binding" as used herein mean that an antibody or capture agent binds to a target such as another antibody, bait biomolecule, or prey biomolecule, with greater affinity than it binds to other molecules under the specified conditions of the invention. In various embodiments of the invention, "specifically binding" may mean that an antibody or capture agent binds to a target analyte molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. Whenever a range appears herein, as in "1-10 or one to ten, the range refers without limitation to each integer or unit of measure in the given range. Thus, by 1-10 it is meant each of 1, 2, 3, 4, 5, 6, 7, 8, 9, 10 and any subunit in between.

As used herein, the term "prey" or "prey biomolecule" or "target prey biomolecule" refers to a target protein, peptide, or polynucleic acid (e.g., DNA, mRNA, tRNA, cDNA) which is present in a selected cell type to be analyzed.

As used herein the term "bait" or "bait biomolecule" refers to an identified protein, peptide, or polynucleic acid which can specifically bind to said prey biomolecule. The binding of the bait biomolecule and the prey biomolecule forms the basis for a detection event. In some embodiments, the bait biomolecule binds specifically to the prey biomolecule with a high affinity. In some embodiments, the high binding affinity can be measured using inhabitation kinetics studies. In some embodiments, the high binding affinity can be less than $10^{-3}$ M (i.e., 0.001 M), $10^{-4}$ M, $10^{-5}$ M, $10^{-6}$ M, $10^{-7}$ M, $10^{-8}$ M, $10^{-9}$ M, $10^{-10}$ M, or less. In some embodiments, the bait biomolecule is an antigen and the prey biomolecule is an antibody. In some embodiments, the bait biomolecule is a first protein and the prey biomolecule is a second protein. In such an embodiment, this invention can be used to measure protein-protein interactions (PPI). In some embodiments, the first and second proteins can independently be selected from an antibody, single chain antibodies, antigen-binding antibody fragments, antigens, receptors, ligands, aptamers, aptamer receptors, polynucleic acid, cell membrane protein, cytokine, transporter protein, cell-signaling molecule, viral particle component, bacterial particle component, or housekeeper protein. In some embodiments, when the prey biomolecule is a polynucleic acid, the bait biomolecule is a polynucleic acid comprising a sequence of which a portion has the reverse complement to a portion of the sequence of the prey biomolecule such that a portion of the bait biomolecule polynucleic acid sequence hybridizes to a portion of the prey biomolecule. In such an embodiment, this invention can be used to detect or isolate selected polynucleic acids from the cells in the sample. In such an embodiment, the prey biomolecule and bait biomolecule can independently be connected to a biotin functional group so as to enable streptavidin-antibody binding by the methods described herein.

As used herein the term "magnetic bead" refers to any having at least some magnetic characteristic, e.g., ferromagnetic, paramagnetic, and superparamagnetic property. In some embodiments, a magnetic bead comprises iron, nickel, cobalt, iron oxide, barium iron oxide, manganese oxide, chromium oxide, cobalt oxide, nickel oxide, cobalt manganese phosphide, or combinations thereof. In some embodiments, the magnetic bead can be coated with a polymer, a hydrogel, polyethyleneglycol (PEG), and/or a functionalized silane. In some embodiments, the magnetic bead can be coated with a layer of silica about the magnetic characteristic-inducing component. In some embodiments, the magnetic bead can be functionalized with carboxylic acid, amine, biotin, streptavidin, avidin, neutravidin, NHS, or maleimide. Methods of preparing magnetic beads are well understood in the art as described in, e.g., U.S. Pat. Nos. 6,773,812 and 6,280,618, the entirety of which are incorporated herein by reference. The magnetic beads can be obtained from commercial vendors (which can include or exclude: Sera-Mag Streptavidin Speedbeads™, Sera-Mag Neutravidin Speedbeads™, Streptavidin-Mag Sepharose®, or Streptavidin-Mag Agarose™ (Cytiva Sciences (formerly GE Healthcare, formerly Amersham Biosciences)); AbraMag Streptavidin Magnetic Beads™ or AbraMag Biotin Magnetic Beads' (Abraxis, Thomas Scientific); Dynabeads™ (Thermo Fisher), MACS® beads (Miltenyi Biotec), or Turbobeads™ (Turbobeads)).

As used herein, the term "primary antibody against bait biomolecule" refers to antibodies, single chain antibodies (which can include or exclude ScFvs, nanobodies, cameloids), antigen-binding antibody fragments, antigens, receptors, ligands, aptamers, aptamer receptors, or polynucleic acids, that binds specifically to the bait biomolecule. In some embodiments, the primary antibody against bait biomolecule is a monoclonal antibody. In some embodiments, the primary antibody against bait biomolecule is a polyclonal antibody.

As used herein, the term "secondary antibody against primary antibody against bait biomolecule" refers to antibodies, single chain antibodies (which can include or exclude ScFvs, nanobodies, or cameloids), antigen-binding antibody fragments, antigens, receptors, ligands, aptamers, aptamer receptors, or polynucleic acids, that specifically binds to a portion of the primary antibody against bait biomolecule. The epitope site of the primary antibody against bait biomolecule to which the secondary antibody binds does not disrupt the binding of the primary antibody against the bait biomolecule. In some embodiments, the secondary antibody against primary antibody against bait biomolecule is connected to a magnetic bead, either directly through chemical conjugation to a functional group on the secondary antibody (which can include or exclude a carboxylic acid, amine, or cysteine of an amino acid of the antibody or synthetically added to the antibody) or indirectly through biotin-streptavidin (or neutravidin or avidin) interactions. In some embodiments, the secondary antibody against primary antibody against bait biomolecule is a monoclonal antibody. In some embodiments, the secondary antibody against primary antibody against bait biomolecule is a polyclonal antibody.

As used herein, the term "primary antibody against prey biomolecule" or "primary antibody against target prey biomolecule" refers to antibodies, single chain antibodies (which can include or exclude ScFvs, nanobodies, or cameloids), antigen-binding antibody fragments, antigens, receptors, ligands, aptamers, aptamer receptors, or polynucleic acids, that specifically bind to the prey biomolecule. In some embodiments, the primary antibody against prey biomolecule binds to an epitope site on the prey biomolecule while the prey biomolecule is interacting with the bait biomolecule. In some embodiments, the prey biomolecule interaction with the bait molecule forms a complex to which a portion of the primary antibody against prey biomolecule binds. In some embodiments, the primary antibody against prey biomolecule is labelled with a fluorophore.

As used herein, the term "secondary antibody against primary antibody against prey biomolecule" refers to antibodies, single chain antibodies (which can include or exclude ScFvs, nanobodies, or cameloids), antigen-binding antibody fragments, antigens, receptors, ligands, aptamers, aptamer receptors, or polynucleic acids, that specifically bind to the primary antibody against prey biomolecule. In some embodiments, the secondary antibody against primary antibody against prey biomolecule is presented to the primary antibody against prey biomolecule while the primary antibody against prey biomolecule is bound to the prey molecule (prey sequential addition). In some embodiments, the secondary antibody against primary antibody against prey biomolecule first binds to an epitope site of the primary antibody against prey biomolecule before the primary antibody against prey biomolecule binds to said prey biomolecule (prey complexed addition). The epitope of the primary antibody against prey biomolecule to which the secondary antibody against primary antibody against prey biomolecule binds is not part of the prey biomolecule-bait biomolecule interaction. In some embodiments, the secondary antibody against primary antibody against prey biomolecule is a monoclonal antibody. In some embodiments, the secondary antibody against primary antibody against prey biomolecule is a polyclonal antibody. In some embodiments, the secondary antibody against primary antibody against prey biomolecule is labelled with a fluorophore.

As used herein, the term "capture agent" refers to a biological molecule which can selectively bind to a target biomolecule. In some embodiments, a capture agent includes antibodies, single chain antibodies (which can include or exclude ScFvs, nanobodies, or cameloids), antigen-binding antibody fragments, antigens, receptors, ligands, aptamers, aptamer receptors, or polynucleic acids, that specifically bind to the prey biomolecule.

As used herein, the term "fluorophore" refers to a moiety which emits a fluorescent signal in response to a light-stimulation event. A fluorophore can be a small molecule compound or a fluoresecent protein. In some embodiments, the fluorophore can be selected from a chemiluminescent fluorophore or fluorescent fluorophore. In some embodiments, the small molecule fluorophore can include or exclude: FAM, Cy dyes, Alexa Fluors, Pacific Blue, Coumarin, BODIPY, Dansyl, Lucifer yellow, rhodamine, Texas Red-X, Pacific Green, Oregon Green, Texas Red, Tetramethylrhodamine, Pacific Orange, eFlours, PE-eFlours, PerCP-eFluors, Super Bright Fluors, DyLight Fluors, StarBright Fluors, DRAQ and CyTRAK probes, EverFluor fluors, Bella Fluors, Atto tags, Abberior Dyes, MegaSTOKES Dyes, DY fluors, HiLyte Fluors, SeTau Dytes, Quasar and Cal Fluors, SureLight Dyes, APC (Allophycocyanin), APCXL, RPE, BPE, YOYO-1, and others described in the 11th Edition of *The Molecular Probes Handbook, A Guide to Fluorescent Probes and Labeling Technologies* by Iain Johnson and Michelle T. Z. Spence published 2010 by Life Technologies Corporation) and *Invitrogen™ Molecular Probes Handbook: A Guide to Fluorescent Probes and Labeling Technologies*, $11^{th}$ edition (Mfr. No. Invitrogen™ H37126), both of which are hereby incorporated by reference in their entirety. The fluorescent fluorophore can be any fluorophore understood in the art and can be attached to the antibody by well-understood methods in the art. In some embodiments, the functionalization of said antibody with the fluorophore can be through NHS chemistry or maleimide chemistry such that said fluorophore is covalently conjugated to said antibody through amines or cysteine residues, respectively. In some embodiments, the fluorescent protein is independently co-expressed with the bait biomolecule, the prey biomolecule, or both. In some embodiments, the fluorescent protein can include or exclude: GFP (green fluorescent protein), YFP (yellow fluorescent protein), CFP (cyan fluorescent protein), RFP (red fluorescent protein), mCherry, mNeon Green, Sirius, Sandercyanin, shBFP-N158S, Azurite, EBFP2, mKalama1, mTagBFP2, TagBFP, shBFP, ECFP, Cerulean, mCerulean3, SCFP3A, CyPet, mTurquise, mTFP1, monomeric Midoriishi-Cyan, Aquamarine, TurboGFP, TagGFP2, mUKG, Superfolder GFP, Emerald, EGFP, Monomeric Azami Green, mWasabi, Clover, NowGFP, mClover3, TagYFP, EYFP, Topaz, Venus, SYFP2, Citrine, Ypet, IanRFP-deltaS83, mPapayal, mCyRFP1, monomeric Kusabira-Orange, mOrange, mOrange2, MOKk, MKO2, TagRFP, TagRFP-T, RRvT, mRuby, mRuby2, mTangerine, mApple, mStrawberry, FusionRed, mNectarine, mRuby3, mScarlet, mScarlet-I, mKate2, HcRed-Tandem, mPlum, mRaspberry, mNeptune, NirFP, TagRFP657, TagRFP675, mCardinal, mStable, mMaroon1, mGarnet2, iFP1.4, iFP713, iFP670, iFP682, iFP702, iFP720, iFP2.0, mIFP, TDsmURFP, miRFP670, Sapphire, T-Sapphire, mAmetrine, mKeima, mBeRFP, LSS-mKate2, LSS-mKate1, LSSmOrange, or CyOFP1.

As used herein the term "lysis buffer" or "cell lysis buffer" refers to an agent which is capable of disrupting the cell membrane. Lysis buffers can comprise denaturing or non-denaturing detergents (also referred to herein as surfactants). Denaturing detergents can be used when the target biomolecule is a polynucleic acid. Non-dentaturing detergents are used when the target biomolecule is a protein or polypeptide whose tertiary structure retention is required for detection. In some embodiments, the denaturing detergent is SDS (sodium dodecyl sulfate). In some embodiments, the non-denaturing detergent is selected from: CHAPS, deoxycholate, Triton™ X-100, NP40, and Tween 20. The lysis buffer can further comprise buffer salts which are well-understood in the art.

In some embodiments, the prey biomolecule and the bait biomolecule are independently selected from cell-surface proteins or cystolic proteins. In some embodiments, the prey biomolecule and the bait biomolecule are independently selected from any protein in The Human Protein Atlas (https://www.proteinatlas.org/, accessed Jun. 26, 2020). In some embodiments, the prey biomolecule and the bait biomolecule are independently selected from: HLA-DR, Kappa, Lambda, Pax-5, BCL-2, Ki-67, ZAP-70, MPO, TdT, FMC-7, HER2, NEU, Prostate stem cell antigen (PSCA), epithelial-specific antigen (ESA), epithelial cell adhesion molecule (EpCAM), a2131, VEGFR-1, VEGFR-2, CD133, AC133 antigen, CD1, CD2, CD3, CD4, CD5, CD6, CD7, CD8, CD9, CD10, CD11a, CD11b, CD11c, CD13, CD14, CD15, CD16, CD19, CD20, CD21, CD22, CD23, CD25, CD30, CD33, CD34, CD38, CD41, C43, CD45, CD56, CD57, CD58, CD61, CD64, C71, CD79a, CD99, CD103, CD117, CD123, CD138, CD138, CD163, CD235a, HLA-DR, Kappa, Lambda, Pax-5, BCL-2, Ki-67, ZAP-70, MPO, TdT, FMC-7, Pro2PSA, ROMA (HE4+CA-125), OVA1 (multiple proteins), HE4, Fibrin/fibrinogen degradation product (DR-70), AFP-L3%, Circulating Tumor Cells (EpCAM, CD45, cytokeratins 8, 18+, 19+), HER2, NEU, Prostate stem cell antigen (PSCA), epithelial-specific antigen (ESA), epithelial cell adhesion molecule (EpCAM), α2β1, VEGFR-1, VEGFR-2, CD133, AC133 antigen, p63 protein, c-Kit, CA19-9, Estrogen receptor (ER), Progesterone receptor (PR), Pro2PSA, HER-2/neu, CA-125, CA15-3, CA27.29, Free PSA, Thyroglobulin, Nuclear Mitotic Apparatus protein (NuMA, NMP22), Alpha-fetoprotein (AFP)b, ROMA (HE4+CA-125), OVAL HE4, DR-70, p63 protein, c-Kit, CA19-9, Total PSA, alpha-Methylacyl-CoA Racemase/AMACR, CA125/MUC16, ER alpha/NR3A1, ER beta/NR3A2, Thymidine Kinase 1, AG-2, BRCA1, BRCA2, CA15-3/MUC-1, Caveolin-1, CD117/c-kit, CEACAM-5/CD66e, Cytokeratin 14, EGF R/ErbBl, HIN-1/SCGB3A1, Ki-67/MKI67, MKP-3, Nestin, NGF R/TNFRSF16, NM23-H1, PARP, PP4, Serpin E1/PAI-1, 14-3-3 beta, 14-3-3 sigma, 14-3-3 zeta, 15-PGDH/HPGD, 5T4, A33, ABCBS, ABCB6, ABCG2, ACE/CD143, ACLP, ACP6, Afadin/AF-6, Afamin, AG-2, AG-3, Akt, Aldo-keto Reductase 1C3/AKR1C3, alpha 1B-Glycoprotein, alpha 1-Microglobulin, AlphaB Crystallin/CRYAB, alpha-Fetoprotein/AFP, alpha-Methylacyl-CoA Racemase/AMACR, AMFR/gp78, Annexin A3, Annexin A8/ANXA8, APC, Apolipoprotein A-I/ApoA1, Apolipoprotein A-II/ApoA2, Apolipoprotein E/ApoE, APRIL/TNFSF13, ASCL1/Mashl, ATBF1/ZFHX3, Attractin, Aurora A, BAP1, Bcl-2, Bcl-6, beta 2-Microglobulin, beta-1,3-Glucuronyltransferase 1/B3GAT1, beta-Catenin, beta-III Tubulin, Bikunin, BMI-1, B-Raf, BRCA1, BRCA2, Brk, C4.4A/LYPD3, CA15-3/MUC-1, c-Abl, Cadherin-13, Caldesmon/CALD1, Calponin 1, Calretinin, Carbonic Anhydrase IX/CA9, Catalase, Cathepsin D, Caveolin-1, Caveolin-2, CBFB, CCR7, CCR9, CEACAM-19, CEACAM-20, CEACAM-4, CHD1L, Chitinase 3-like 1, Cholecystokinin-B R/CCKBR, Chorionic Gonadotropin alpha Chain (alpha HCG), Chorionic Gonadotropin alpha/beta (HCG), CKAP4/p63, Claudin-18, Clusterin, c-Maf, c-Myc, Coactosin-like Protein 1/Cothl, COMMD1, Comulin, Cortactin, COX-2, CRISP-3, CTCF, CTL1/SLC44A1, CXCL17/VCC-1, CXCL8/IL-8, CXCL9/MIG, CXCR4, Cyclin A1, Cyclin A2, Cyclin D2, Cyclin D3, CYLD, Cyr61/CCN1, Cytokeratin 14, Cytokeratin 18, Cytokeratin 19, DAB2, DCBLD2/ESDN, DC-LAMP, Dkk-1, DLL3, DMBT1, DNMT1, DPPA2, DPPA4, E6, E-Cadherin, ECM-1, EGF, EGF R/ErbBl, ELF3, ELTD1, EMMPRIN/CD147, EMP2, Endoglin/CD105, Endosialin/CD248, Enolase 2/Neuron-specific Enolase, EpCAM/TROP1, Eps15, ER alpha/NR3A1, ER beta/NR3A2, ErbB3/Her3, ErbB4/Her4, ERCC1, ERK1, ERK5/BMK1, Ets-1, Exostosin 1, EZH2, Ezrin, FABP5/E-FABP, Fascin, FATP3, FCRLA, Fetuin A/AHSG, FGF acidic, FGF basic, FGF R3, FGF R4, Fibrinogen, Fibroblast Activation Protein alpha/FAP, Follistatin-like 1/FSTL1, FOLR1, FOLR2, FOLR3, FOLR4, FosB/GOS3, FoxMl, FoxO3, FRAT2, FXYD5/Dysadherin, GABA-A R alpha 1, GADD153, GADD45 alpha, Galectin-3, Galectin-3BP/MAC-2BP, gamma-Glutamylcyclotransferase/CRF21, Gasl, Gastrin-releasing Peptide R/GRPR, Gastrokine 1, Gelsolin/GSN, GFAP, GLI-2, Glutathione Peroxidase 3/GPX3, Glypican 3, Golgi Glycoprotein 1/GLG1, gp96/HSP90B1, GPR10, GPR110, GPR18, GPR31, GPR87, GPRC5A, GPRC6A, GRP78/HSPA5, HE4/WFDC2, Heparanase/HPSE, Hepsin, Her2, HGF R/c-MET, HIF-2 alpha/EPAS1, HIN-1/SCGB3A1, HLA-DR, HOXB13, HOXB7, HSP70/HSPA1A, HSP90, Hyaluronidase 1/HYAL1, ID1, IgE, IGFBP-2, IGFBP-3, IGFBP-4, IGFBP-6, IGF-I, IGF-I R, IGF-II, IGFL-3, IGFLR1, IL-1 beta/IL-1F2, IL-17E/IL-25, IL-2, IL-6, IMP Dehydrogenase 1/IMPDH1, Importin alpha 2/KPNA2, ING1, Integrin beta 1/CD29, Integrin beta 3/CD61, IQGAP1, Isocitrate Dehydrogenase 1/IDH1, ITIH4, ITM2C, Jagged 1, JNK, JunB, JunD, Kallikrein 2, Kallikrein 6/Neurosin, KCC2/SLC12A5, Ki-67/MKI67, KiSS1R/GPR54, KLF10, KLF17, L1CAM, Lactate Dehydrogenase A/LDHA, Lamin B1, LEF1, Leptin/OB, LIN-28A, LIN-28B, Lipocalin-2/NGAL, LKB1/STK11, LPAR3/LPA3/EDG-7, LRMP, LRP-1B, LRRC3B, LRRC4, LRRN1/NLRR-1, LRRN3/NLRR-3, Ly6K, LYPD1, LYPD8, MAP2, Matriptase/ST14, MCAM/CD146, M-CSF, MDM2/HDM2, Melan-A/MART-1, Melanocortin-1 R/MC1R, Melanotransferrin/CD228, Melatonin, Mer, Mesothelin, Metadherin, Metastin/KiSS1, Methionine Aminopeptidase, Methionine Aminopeptidase 2/METAP2, MFAP3L, MGMT, MIA, MIF, MINA, Mind Bomb 2/MIB2, Mindin, MITF, MKK4, MKP-1, MKP-3, MMP-1, MMP-10, MMP-13, MMP-2, MMP-3, MMP-8, MMP-9, MRP1, MRP4/ABCC4, MS4A12, MSH2, MSP R/Ron, MSX2, MUC-4, Musashi-1, NAC1, Napsin A, NCAM-1/CD56, NCOA3, NDRG1, NEK2, NELL1, NELL2, Nesfatin-1/Nucleobindin-2, Nestin, NFkB2, NF-L, NG2/MCSP, NGF R/TNFRSF16, Nicotinamide N-Methyltransferase/NNMT, NKX2.2, NKX3.1, NM23-H1, NM23-H2, Notch-3, NPDC-1, NTS1/NTSR1, NTS2/NTSR2, OGR1, Olig2, Osteopontin/OPN, Ovastacin, OXGR1/GPR80/P2Y15, p130Cas, p15INK4b/CDKN2B, p16INK4a/CDKN2A, p18INK4c/CDKN2C, p21/CIP1/CDKN1A, p27/Kipl, P2X5/P2RX5, p53, PARP, PAUF/ZG16B, PBEF/Visfatin, PDCD4, PDCD5, PDGF R alpha, PDGF R beta, PDZD2, PEA-15, Pepsinogen A5/PGAS, Peptidase Inhibitor 16/PI16, Peroxiredoxin 2, PGCP, PI 3-Kinase p85 alpha, PIWIL2, PKM2, PLK1, PLRP1, PP4, P-Rexl, PRMT1, Profilin 1, Progesterone R B/NR3C3, Progesterone R/NR3C3, Progranulin/PGRN, Prolactin, Prostaglandin E Synthase 2/PTGES2, PSAP, PSCA, PSMA/FOLH1/NAALADase 1, PSMA1, PSMA2, PSMB7, PSP94/MSMB, PTEN, PTEN, PTH1R/PTHR1, PTK7/CCK4, PTP beta/zeta/PTPRZ, Rab25, RARRES1, RARRES3, Ras, Reg4, Ret, RNF2, RNF43, S100A1, S100A10, S100A16, S100A2, S100A4, S100A6, S100A7, S100A9, S100B, S100P, SART1, SCUBE3, Secretin R, Serpin A9/Centerin, Serpin E1/PAI-1, Serum Amyloid A1, Serum Amyloid A4, SEZ6L, SEZ6L2/BSRP-A, Skp2, SLC16A3, SLC45A3/Prostein, SLC5A5, SLC5A8/SMCT1, SLC7A7, Smad4, SMAGP, SOCS-1, SOCS-2, SOCS-6, SOD2/Mn-SOD, Soggy-1/ DkkL1, SOX11, SOX17, SOX2, SPARC, SPARC-like 1/SPARCL1, SPINK1, Src, STEAP1, STEAP2, STEAP3/ TSAP6, STRO-1, STYK1, Survivin, Synaptotagmin-1, Syndecan-1/CD138, Syntaxin 4, Synuclein-gamma, Tankyrase 1, Tau, TCF-3/E2A, TCL1A, TCL1B, TEM7/PLXDC1, TEM8/ANTXR1, Tenascin C, TFF1, TGF-beta 1, TGF-beta 1, 2, 3, TGF-beta 1/1.2, TGF-beta 2/1.2, TGF-beta RI/ALK-5, THRSP, Thymidine Kinase 1, Thymosin beta 10, Thymosin beta 4, Thyroglobulin, TIMP Assay Kits, TIMP-1, TIMP-2, TIMP-3, TIMP-4, TLE1, TLE2, TLR2, TM4SF1/ L6, TMEFF2/Tomoregulin-2, TMEM219, TMEM87A, TNF-alpha, TOP2A, TopBP1, t-Plasminogen Activator/tPA, TRA-1-60(R), TRA-1-85/CD147, TRAF-4, Transgelin/TAGLN, Trypsin 2/PRSS2, Tryptase alpha/TPS1, TSPAN1, UBE2S, uPAR, u-Plasminogen Activator/Urokinase, Urotensin-II R, VAP-1/A0C3, VCAM-1/CD106, VEGF, VEGF R1/Flt-1, VEGF R2/KDR/Flk-1, VEGF/P1GF Heterodimer, VSIG1, VSIG3, YAP1, ZAG, ZAP70, ZMIZ1/Zimp10, and Carcino-embryonic antigen.

In some embodiments, the prey biomolecule is selected from biomolecules expressed by kidney cells, infectious or parasitic agents, solid tumor cells, circulating tumor cells, or any other cell useful for diagnosis or prognosis. In some embodiments, the prey biomolecule is selected from biomoelcules expressed on the surface or within kidney cells, infectious agents (e.g., bacteria or virus), solid tumor cells, or circulating tumor cells. In some embodiments, the prey biomolecules expressed on the surface or within kidney cells can include or exclude: KIM-1, Albumin, beta-2 microglobulin, Cystatin C, Clusterin, Apolipoprotein A-I/ApoA1, CXCL8/IL-8, ERCC1, Ki-67/MKI67, MMP-9, or Trefoil factor-3.

In some embodiments, the prey biomolecule is one or a plurality of biomarkers for a particular type of cancer. In some embodiments, the prey biomolecule for breast cancer can include or exclude her2-neu, ER, PR, Ki-67, and p53. In some embodiments, the prey biomolecule for lung cancer can include or exclude TTF-1, Napsin A, CK 5/6, p40/63, and Synaptophosmin. In some embodiments, the prey biomolecule for prostrate cancer can include or exclude AMACR, PSA, CEA, and p63. In some embodiments, the prey biomolecule for colorectal cancer can include or exclude MLH1, MSH2, PMS2, MSH6, c-Kit, p16, and BRAF V600E. In some embodiments, the prey biomolecule for tumor infiltrating lymphocytes can include or exclude CD4, CD8, CD14, CD20, CD45RO, FoxP3, PD-L, and PD-L1. In some embodiments, the prey biomolecule for cancers of the urinary system (bladder, kidney, urethra) can include or exclude CK7, p63, CK20, p53, Ki-67, PSA, Vimentin, and PAX8.

In some embodiments, the prey biomolecule is cell-specific. The cells can be in a healthy state (normal) or diseased state (abnormal). Monocytes and macrophages can exhibit a prey biomolecule that includes or excludes the CD14 and CD16 biomolecules. Lymphocyte B cells can exhibit a prey biomolecule that includes or excludes the CD20 biomolecule. Lymphocyte NK cells can exhibit a prey biomolecule that includes or excludes the CD56 biomolecule. Lymphocytes T cells can exhibit a prey biomolecule that includes or excludes the CD3 biomolecule. T Reg cells can exhibit a prey biomolecule that includes or excludes the CD4, CD25, and FoxP3 biomolecule. Cytotoxic T cells can exhibit a prey biomolecule that includes or excludes the CD8 biomolecule. Helper T cells can exhibit a prey biomolecule that includes or excludes the CD4 biomolecule. Naïve T cells can exhibit a prey biomolecule that includes or excludes the CD45RA biomolecule. Memory T cells can exhibit a prey biomolecule that includes or excludes the CD45R0 biomolecule. Tth cells can exhibit a prey biomolecule that includes or excludes the CXRS biomolecule. Th17 cells can exhibit a prey biomolecule that includes or excludes the CCR6 biomolecule. Th2 cells can exhibit a prey biomolecule that includes or excludes the CCR4 biomolecule. Th1 cells can exhibit a prey biomolecule that includes or excludes the CXCR3 biomolecule. Tumor cells can exhibit a prey biomolecule that includes or excludes the PanCK biomolecule.

As used herein, the term "antibody" refers to a protein that can specifically bind to an antigen. In some embodiments, an antibody can include or exclude any recombinant or naturally occurring immunoglobulin molecule which can include or exclude a member of the IgG class (e.g. IgG1), IgM class, IgY class, IgD class, IgE class, and also any antigen binding immunoglobulin fragment, which can include or exclude Fv, Fab and F(ab')2 fragments, antibody fragment, ScFv (single-chain variable fragment, a fusion protein of the variable regions of the heavy ($V_H$) and light chains ($V_L$) of immunoglobulins, connected with a short linker peptide of ten to about 25 amino acids), or single-domain antibody (nanobody), and any derivatives thereof. In embodiments, the antibody can be a monoclonal or polyclonal antibody.

The term "antibody fragments" as used herein, refers to a portion of an intact antibody, wherein the portion retains at least one, and as many as most or all, of the functions normally associated with that portion when present in an intact antibody. In some embodiments, an antibody fragment comprises an antigen binding site of the intact antibody and thus retains the ability to bind antigen. In some embodiments, an antibody fragment, for example one that comprises the Fc region, retains at least one of the biological functions normally associated with the Fc region when present in an intact antibody, which can include or exclude FcRn binding, antibody half-life modulation, ADCC function and complement binding. In some embodiments, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

"Polyclonal Antibodies" or "PAbs," are heterogeneous populations of antibody molecules derived from the sera of animals immunized with an antigen, or an antigenic functional derivative thereof. For the production of polyclonal antibodies, host animals which can include or exclude rabbits, mice and goats, may be immunized by injection with an antigen or antigen-conjugate, optionally supplemented with adjuvants. Polyclonal antibodies may be unpurified, purified or partially purified from other species in an antiserum. The techniques for the preparation and purification of polyclonal antibodies are described in various general and more specific references, including but not limited to Kabat & Mayer, *Experimental Immunochemistry*, 2d ed., (Thomas, Springfield, Ill. (1961)); Harlow & Lane, *Antibodies: A Laboratory Manual* (Cold Spring Harbor Laboratory Press, Cold Spring Harbor, N.Y. (1988)); and Weir, *Handbook of Experimental Immunology*, 5th ed. (Blackwell Science, Cambridge, Mass. (1996)).

"Monoclonal antibodies," or "MAbs," are homogeneous populations of antibodies to a particular antigen and may be obtained by any technique that provides for the production of antibody molecules, which can include or exclude by continuous culture of cell lines. These techniques include, but are not limited to the hybridoma technique of Kohler and Milstein, "Continuous cultures of fused cells secreting antibiody of predefined specificity," Nature, 256:495-497 (1975); and U.S. Pat. No. 4,376,110), the human B-cell hybridoma technique (Kozbor, et al., "The Production of Monoclonal Antibodies From Human Lymphocytes," Immunology Today, 4:72-79 (1983); Cote, R. J., et al., "Generation of human monoclonal antibodies reactive with cellular antigens," Proc. Natl. Acad. Sci. USA, 80:2026-30 (1983)), and the EBV-hybridoma technique (Cole, et al., in Monoclonal Antibodies And Cancer Therapy, Alan R. Liss, Inc., New York, pp. 77-96 (1985)). Such antibodies may be of any immunoglobulin class including IgG, IgM, IgE, IgA, IgD and any subclass thereof. The hybridoma producing the MAb of this invention may be cultivated in vitro or in vivo. Production of high titers of MAbs in vivo makes this a presently preferred method of production.

Alternatively, techniques described for the production of single chain antibodies (U.S. Pat. No. 4,946,778; Bird, et al., "Single-chain Antigen-Binding Proteins," Science, 242:423-426 (1988); Huston, et al., "Protein Engineering of Antibody Binding Sites: Recovery of Specific Activity in an Anti-Digoxin Single-Chain Fv Analogue Produced in *Escherichia coli,*" Proc. Natl. Acad. Sci. USA, 85:5879-83 (1988); and Ward, et al., "Binding Activities of a Repertoire of Single Immunoglobulin Variable Domains Secreted from *Escherichia Coli,*" Nature, 334:544-546 (1989)) can be adapted to produce gene-single chain antibodies suitable for use in the invention. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')2 fragments that can be produced by pepsin digestion of the antibody molecule and the Fab fragments that can be generated by reducing the disulfide bridges of the F(ab')2 fragments. Alternatively, Fab expression libraries may be constructed (Huse, et al., "Generation of a large combinatorial library of the immunoglobulin repertoire in phage lambda," Science, 246:1275-1281 (1989)) to allow rapid and easy identification of monoclonal Fab fragments with the desired specificity.

As used herein, the terms "polypeptide," "peptidomimetic" and "mimetic" include synthetic or genetically engineered chemical compounds that may have substantially the same structural and functional characteristics of protein regions which they mimic.

Polypeptides may, in some embodiments, be modified or unmodified. Generally, peptidomimetics are structural or functional mimics (e.g., identical or similar) to a paradigm polypeptide (i.e., a polypeptide that has a biological or pharmacological function or activity), but can also have one or more peptide linkages optionally replaced by a linkage selected from the group consisting of, for example, —CH$_2$NH—, —CH$_2$—CH$_2$—, —CH═CH— (cis and trans), —COCH$_2$—, —CH(OH)CH$_2$—, and —CH$_2$SO—. The mimetic can be either entirely composed of natural amino acids, synthetic chemical compounds, non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity.

As used herein, the term "about" is intended to qualify the numerical values that it modifies, denoting such a value as variable within a margin of error. When no particular margin of error (such as, for example, standard deviation to a mean value) is recited, the term "about" means plus or minus 10% of the numerical value sf of the number with which it is being used. For example, "about 50%" means in the range of 45% to 55%.

Systems

In some embodiments, this disclosure provides for systems for isolating single cells and analyzing selected cell components. In some embodiments, the systems described herein can analyze the selected cell components quantitatively, with signal-to-noise (SN) ratios higher than 10, higher than 12, higher than 15, or higher than 20.

The combination of single-cell isolation, single-cell lysis, antibody/capture-agent-coated beads, and TIRF or confocal microscopy allows for the sensitive detection of selected cell components. Moreover, the design of targeting bait biomolecules, then forming a complex between bait biomolecules and prey biomolecules followed by imaging by the methods described herein, allows for the capture and analysis of bait-prey biomolecule interactions (protein-protein interactions, PPI) which could not otherwise be detected at such high SN levels.

Substrates

The invention described herein include the use of a substrate comprising a plurality of micron-sized features for the analysis of isolated single cells and/or selected components thereof. In some embodiments, the coverslip can be made of a transparent solid medium. The transparent solid medium can be selected from glass (e.g., pyrex, borosilicate, soda lime, optical glass, quartz), cyclo olefin polymer (e.g., zeonor, zeonex), or polyacrylates. In some embodiments, the substrate can be a coverslip of the type #0 to #4 (corresponding to a thickness of about 0.085 mm to about 0.64 mm). In some embodiments, the substrate can be coated. The coating can include or exclude silanes, polysilanes, or polymers. In some embodiments, the substrate is coated with polydimethyldichlorosilane. The micron-sized features can be etched into the substrate or presented on top of the substrate by a hardened polymer. In some embodiments, the hardened polymer can include or exclude PDMS or SU8. SU-8 comprises Bisphenol A Novolac epoxy monomer that is dissolved in an organic solvent (gamma-butyrolactone GBL or cyclopentanone, depending on the formulation) and crosslinked with a photoacid generator than can include or exclude Triarylsulfonium/hexafluoroantimonate salt. In some embodiments, the hardened polymer can be made from a solid negative master template generated by conventional photolithography methods. The precursor to the hardened polymer and crosslinker is contacted with the negative master template, the cross-linking reaction begun (e.g., heat and/or light), and the master removed to generate the micron-sized features.

Figure 6A:
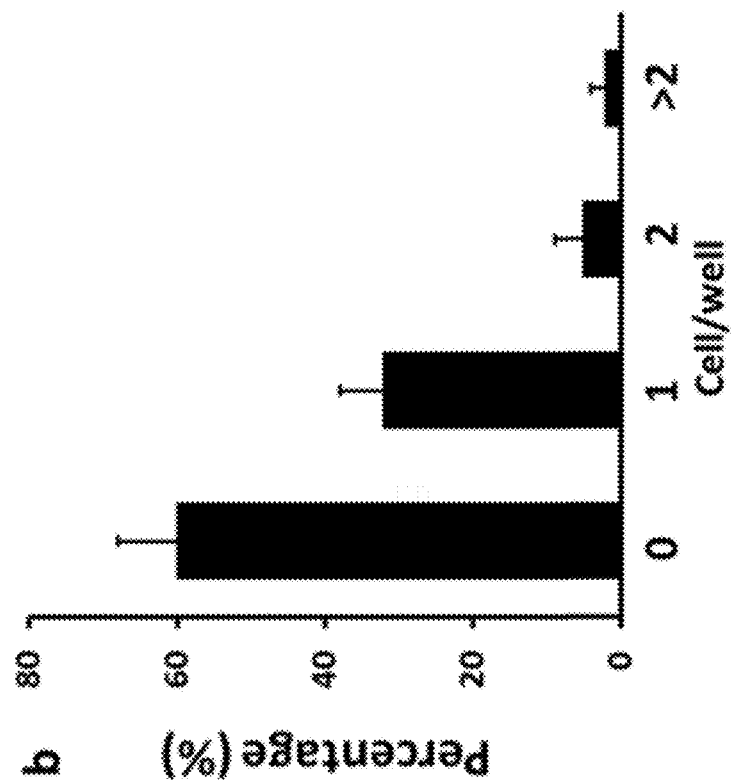
FIGS. 6a & 6b show the number of cells per microwell. 300 ul suspended cells in PBS (about 106 cells/ml) was applied to the surface of the microwell chip (see more details in the "Methods").
Figure 6B:
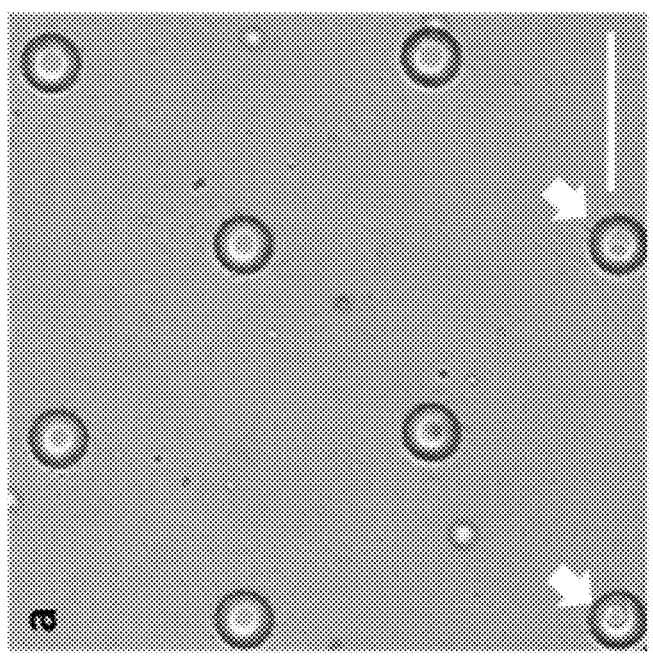

The diameter of the features can be configured so as to allow for one cell to enter each feature. As shown in FIGS. 6A & 6B, the size of the features can be configured so as to selectively isolate one cell per feature. This single-cell isolation allows for, inter alia, the isolation of the cellular components of the isolated cell. In combination with functionalized beads which are co-located with the isolated cells and a platform for enabling high-sensitivity fluorescence detection (e.g., TIRF or confocal microscopy), one or a plurality of the isolated cell's components can be analyzed, including protein-protein interactions. The isolation of single cells also allows for the analysis of rare cells, which can include or exclude hair cells (e.g., cochlear cells), circulating tumor cells, or circulating embryonic cells. The plurality of micron-sized features in the substrate can have features which are round in shape. The plurality of micron-sized features in the substrate can comprise a series of features which are independently of a size with a mean average diameter between 8 microns to 15 microns, 15 microns to 45 microns, 45 microns to 80 microns, 80 microns to 100 microns, 100 microns to 150 microns, or any range between the aforementioned ranges. In some embodiments, the feature diameter can be configured to isolate selected cells (e.g., small cells within a large cell/small cell population). In some embodiments, the mean average diameter of the features can be 15 microns, 16 microns, 17 microns, 18 microns, 19 microns, 20 microns, 21 microns, 22 microns, 23 microns, 24 microns, 25 microns, 26 microns, 27 microns, 28 microns, 29 microns, 30 microns, 31 microns, 32 microns, 33 microns, 34 microns, 35 microns, 36 microns, 37 microns, 38 microns, 39 microns, 40 microns, 41 microns, 42 microns, 43 microns, 44 microns, or 45 microns. The plurality of features can be spaced apart far enough such that the fluorescence bloom from the fluorophore in any one feature will not overlap with the fluorescence bloom from the fluorescence from a fluorophore in another feature. In some embodiments, the mean average distance between the center of each feature can range from about 10 microns to about 5000 microns. The mean average distance between the center of each feature can range from 10 microns to 100 microns, 100 microns to 200 microns, 200 microns to 500 microns, 500 microns to 1000 microns, 1000 microns to 2000 microns, 2000 microns to 5000 microns, or any range between the aforementioned ranges. The depth of the feature can be sufficient to isolate and maintain a single cell within a feature, while preventing two or more cells to occupy the same feature. In some embodiments, the mean average depth of the features can range from about 15 microns to about 150 microns. In some embodiments, the mean average depth of the features can range from about 15 microns to about 40 microns, about 40 microns to about 60 microns, about 60 microns to about 75 microns, about 75 microns to about 90 microns, about 90 microns to about 120 microns, about 120 microns to about 150 microns, or any range between the aforementioned ranges.

Beads

The invention described herein involve the use of nanometer-sized functionalized beads. The size of the bead is such that a plurality of beads will enter the features (wells) of the substrate. The size of the nanometer-sized beads can be from 5 nanometers to 1000 nanometers. In some embodiments, the mean average diameter of the beads can be from 5 nanometers to 20 nanometers, 20 nanometers to 50 nanometers, 50 nanometers to 100 nanometers, 100 nanometers to 500 nanometers, 500 nanometers to 1000 nanometers, or between any of the aforementioned ranges. The beads can be coated with a polymer, silica, or hydrogel layer. The beads can be functionalized to allow for binding to an antibody or capture agent. The beads can be functionalized with carboxylic acid, amine, biotin, streptavidin, avidin, neutravidin, NHS, or maleimide. The functionalized beads can be coated with a biomolecule via a direct covalent bond (e.g., NHS-functionalized bead with a lysine residue on a polypeptide or antibody or 5' amino-functionalized polynucleic acid), or by indirect (e.g., NTA-Ni functionalized bead to a hexa-Histidine modified protein).

In some embodiments, the nanometer-sized functionalized beads can be functionalized by using streptavidin-biotin binding. In some embodiments, nanometer-sized particles coated with a carboxylic acid functional group can be activated with EDC/NHS (1-Ethyl-3-(3-dime thylaminopropyl)carbodiimide/N-hydroxy-succinimide), followed by a wash to yield an EDC-functionalized nanoparticle. Other amide coupling agents can be used instead of EDC, for example, DCC (dicyclohexylcarbodiimide), EDAC.HCl, (N-(3-Dimethylaminopropyl)-N'-ethylcarbodiimide.HCl), HOBt (1-Hydroxybenzotriazole), HOOBt (HODhbt) (Hydroxy-3,4-dihydro-4-oxo-1,2,3-benzotriazine), HOAt (1-Hydroxy-7-aza-1H-benzotriazole), DMAP (4-(N,N-Dimethylamino)pyridine), BOP (Benzotriazol-1-yloxy-tris(dimethylamino)-phosphonium hexafluorophosphate), PyBOP (Benzotriazol-1-yloxy-tripyrrolidinophosphonium hexafluorophosphate), PyOxim (Ethyl cyano(hydroxyimino)acetato-O2)-tri-(1-pyrrolidinyl)-phosphonium hexafluorophosphate), PyBrOP (7-Aza-benzotriazol-1-yloxy-tripyrrolidinophosphonium hexafluorophosphate), DEPBT (3-(Diethoxy-phosphoryloxy)-1,2,3-benzo[d]triazin-4(3H)-one), TBTU/HBTU (2-(1H-Benzotriazol-1-yl)-N,N,N',N'-tetramethylaminium tetrafluoroborate/hexafluorophosphate), HCTU ((2-(6-Chloro-1H-benzotriazol-1-yl)-N,N,N',N'-tetramethylaminium hexafluorophosphate), HDMC (N-[(5-Chloro-1H-benzotriazol-1-yl)-dimethylamino-morpholino]-uronium hexafluorophosphate N-oxide), HATU (2-(7-Aza-1H-benzotriazol-1-yl)-N,N,N',N'-tetramethylaminium hexafluorophosphate), COMU (1-[1-(Cyano-2-ethoxy-2-oxoethylideneaminooxy)-dime thylamino-morpholino]-uronium hexafluorophosphate), TOTT ((2-(1-Oxy-pyridin-2-yl)-1,1,3,3-tetramethylisothiouronium tetrafluoroborate), TFFH (Tetramethylfluoroformamidinium hexafluorophosphate), EEDQ (N-Ethoxycarbonyl-2-ethoxy-1,2-dihydroquinoline), T3P (2-Propanephosphonic acid anhydride), DMTMM (4-(4,6-Dimethoxy-1,3,5-triazin-2-yl)-4-methylmorpholinium salt), or CDI (1,1'-Carbonyldiimidazole). In some alternative embodiments, the coupling can be performed in the presence of a base. The base can be organic or inorganic. The inorganic bases can include or exclude, for example, carbonate buffer, or phosphate buffer. The organic bases can be triethylamine, Diisopropylethylamine (DIPEA), or N-methylmorpholine (NMM).

The wash can be a pH mild wash so as to not hydrolyze the NHS moieties. The mild pH wash can be with PBS buffer (phosphate buffered saline, pH around 7.4). Next, streptavidin can be reacted with the EDC-functionalized nanoparticle to yield a streptavidin-functionalized nanoparticle. Other avidin-like molecules can be used in place of streptavidin, for example: avidin, neutravidin, superavidin, and streptavidin with one, two or three biotins already bound. In some embodiments, the capture agent/antibody can be functionalized with a biotin. The antibody can be reacted with a cross-linker, such as Sulfo-SMCC (Pierce) followed by a thiol-conjugated biotin to yield a biotinylated antibody. In an alternative embodiment, the antibody can be reacted with a NHS-conjugated biotin, where the NHS-conjugated biotin can react with any free amine on the antibody (prefeable, free amines from lysine residues) to yield a biotinylated antibody. In an alternative embodiment, the antibody can be reacted with DTT (dithioerithritol) to break the di-thiol cysteine bond to yield a free sulfuryl hydryl group. The sulfuryl hydryl group can be reacted with a maleimide-conjugated biotin to yield a biotinylated antibody. In some embodiments, the nanoparticle can be purchased with a functional group selected from: carboxylic acid, NHS, streptavidin, amine, alkyne, or aldehyde. The biotinylated antibody can be reacted to the streptavidin-functionalized nanoparticle to create the directly-linked antibody-functionalized nanoparticle.

Each nanometer-sized functionalized bead is homogeneously functionalized with the same biomolecule. However, in some embodiments, a plurality of types of homogeneously-functionalized nanometer-sized beads can be added to the micron-sized substrate features to enable the capture and analysis of a plurality of prey biomolecules within the same cell. In some embodiments, the relative amounts of each species of the plurality of types of homogeneously-functionalized nanometer-sized beads can be added to the micron-sized substrate features to enable relative quantitation of the various cell components in the same isolated cell.

In some embodiments, the nanometer-sized functionalized beads are functionalized with a single capture agent or antibody (primary antibody to bait protein). In some embodiments, the nanometer-sized functionalized beads are functionalized with a second antibody, and the first antibody is to a portion of the second antibody. In some embodiments, the second antibody is against the bait biomolecule. Such a configuration allows for the programmability of functionalized beads to a bait biomolecule by adding identified antibodies to a first antibody-functionalized bead.

In some embodiments, a capture agent/antibody can be added to the nanometer-sized functionalized beads before the bead is presented to the substrate comprising a plurality of micron-sized features, or after the nanometer-sized functionalized bead is presented to the micron-sized feature. In some embodiments, the plurality of antibody-coated beads can comprise a plurality of secondary antibodies against the primary antibodies against the target bait biomolecules. The plurality of antibody-coated beads can comprise a plurality of primary antibodies against the target bait biomolecules. In some aspects, the plurality of antibody-coated beads can comprise a secondary antibody to the plurality of primary antibodies to a bait biomolecule. In some embodiments, the capture agent/antibody can be added to a solution comprising the cells before the cells are presented to the substrate comprising a plurality of micron-sized features. In such an embodiment, the antibodies can associate to cell-surface cellular components in free solution, before the antibodies are connected to the nanometer-sized functionalized bead, which may increase reaction kinetics.

The nanometer-sized functionalized beads (further functionwalized with a capture agent/antibody) can be added to the substrate comprising a plurality of micron-sized features before or after presentation of a plurality of cells to the substrate. In some beads can have a magnetic property, such that introduction of a magnetic field will pull the beads to the surface of the substrate, so as to allow for more efficient sensitivity of fluorescence detection when using TIRF or confocal microscopy. In some embodiments, the beads can be pulled down to the substrate surface using gravitational force (e.g., allowing for sedimentation time, or presenting the substrate to high gravitational force in a centrifuge configured to accept the planar substrate). In some embodiments, the magnetic force is applied before, or after, the cells are presented to the substrate comprising a plurality of micron-sized features. In some embodiments, the capture agent/antibody is added to the nanometer-sized functionalized beads which is first added to the substrate comprising a plurality of micron-sized features.

In some embodiments, the system can further comprise one or a plurality of types of cells. The type of cells can be rare cells, which can include or exclude hair cells (e.g., cochlear cells), circulating tumor cells, or circulating embryonic cells. Cochlear cells cannot be measured by standard cell-sampling methods because most cell analysis methods do not allow for the analysis of the minuscule amount of cochlear cells ($10^4$ from an entire human cochlea) because of their lack of sensitivity. The high SN (signal-to-noise ratio) single-cell component analysis systems and methods of this disclosure also allow for the detection of circulating tumor cells at an early stage of cancer, where the tumor cells would not normally be otherwise detectable. In some embodiments, the high SN single-cell component analysis systems and methods of this disclosure also allow for the detection of circulating embryonic cells in a female who is or was pregnant. The circulating embryonic cells can be microchimeric fetal cells. Microchimerical cells are often found in females after birth and can be attributed to enhanced immune systems (Dawe, et al., "Cell Migration from Baby to Mother," *Cell Adh Migr.* 2007 January-March; 1(1): 19-27).]

In some embodiments, the cells can be from a subject. Cells from a subject can comprise biomolecules which may be useful to assist in identifying the cellular state, identity, growth rate, lineage, mutations, variants, expression levels, cancer stage or remission status, and/or latent or active infection. Such cells may include or exclude, for example, mammalian cells, immunomodulatory cells, lymphocytes, monocytes, polymorphs, T cells, tumor cells, yeast cells, bacterial cell, infectious agents, parasites, plant cells, transfected cells such as NSO, CHO, COS, 293 cells.

In some embodiments, the cell may be alive, dead, fixed and/or substantially intact. In some embodiments, the cells can be the same type or different types. When the cells are different types, the cells can be from different tissue or tumor origin, exhibit a different pathology, express different or mutated biomolecules, express different levels of biomolecules, express biomolecules with different post-translational modifications, or exhibit different morphology. In some embodiments, the capture agent/antibody is capable of distinguishing between a mutant biomolecule and a wild-type biomolecule. When the cells are from different tumor origin, the cells can be from a tumor which can include or exclude, for example, breast cancer, lung cancer, prostate cancer, bone cancer, colorectal cancer, liver cancer, pancreatic cancer, thyroid cancer, bladder cancer, or other types of cancer.

In some embodiments, the cells can comprise one or a plurality of a type of target prey biomolecule. When a plurality of types of target prey biomolecules are to be detected, a plurality of types of nanometer-sized functionalized beads with a plurality of types of antibodies corresponding to the baits corresponding to the prey biomolecules can be used.

In some embodiments, the plurality of target prey biomolecules can comprise biomolecules which can be found in the cell membrane of said cells. In some embodiments, the plurality of target prey biomolecules can comprise biomolecules which can be found in the cytoplasm of said cells. In some embodiments, the bait biomolecules and prey biomolecules can be independently selected from: proteins, DNA, RNA, mRNA, tRNA, cRNA, antibodies, antibody fragments, ScFv's, peptides, and small molecules. The DNA or RNA can be further modified with biotin. The systems and methods described herein can enable single-cell sequencing, where the prey biomolecule is DNA or RNA from the isolated cell. In some embodiments, the captured DNA or RNA as prey biomolecule can be dehybridized from the corresponding bait polynucleotide sequence using heat or a denaturing agent (e.g., low salt, DMSO, urea, formamide, etc.) and the dehybridized DNA or RNA can be further analyzed by DNA analysis methods to determine a portion or all of the sequence of said DNA or RNA. In some embodiments, the DNA analysis method can include or exclude: DNA sequencing, qPCR, SSCP, STR, or genotyping by microarray or mass spectrometry. The DNA sequencing methods can include or exclude the use of the Illumina HiSeq, MiSeq, iSeq, or NovaSeq; the ThermoFisher IonTorrent system; the Qiagen GeneReader system; or the BGI DNBSEQ-T7, DNBSEQ-G400, DNBSEQ-50 systems using the manufacturer's provided protocols and instructions.

In some embodiments, the system further comprises a cell membrane disruption agent to release the cellular components. The cell membrane disruption agent can be a lysis buffer. The lysis buffer can include or exclude denaturing detergents (when analyzing polynucleotides) or non-denaturing detergents (when analyzing proteins, antibodies, and polypeptides). In some embodiments, the denaturing detergent is SDS (sodium dodecyl sulfate). In some embodiments, the non-denaturing detergent is selected from: CHAPS, deoxycholate, Triton™ X-100, NP40, and Tween 20. The lysis buffer can further comprise buffer salts which are well-understood in the art.

In some embodiments, the system and methods glass substrate can be configured to be measureable with TIRF (total internal reflectance specstroscopy). TIRF illumination can eliminate or reduce the scatter from other light scattering elements on the substrate surface. TIRF illumination offers the advantage that illumination and fluorescence will not interact be affected by surface debris. TIRF microscopy in the present disclosure reduces background fluorescence from outside the focal plane and can noticeably improve the signal-to-noise ratio of the fluorescence light emitted from the fluorophores which are connected to the prey biomolecule-bait biomolecule/antibody complex. TIRF microscopy utilizes an induced evanescent wave in a limited substrate region immediately adjacent to the interface between two media having different refractive indices. In some embodiments, the utilized TIRF interface can be the contact area between the substrate and a glass coverslip. In some embodiments, the illuminated system can comprise optical fibers to deliver light to the edge to the slide. In some embodiments, the illuminated system can comprise the Darklite Vertical Illuminator (Micro Video Instruments, Inc, Avon, Mass.).

Methods

The invention provides, inter alia, methods for identifying a biomolecule-biomolecule interaction, comprising the steps: (a) contacting one or a plurality of cell types with a system of as described herein, (b) presenting a lysis buffer to the system, and (c) imaging the system by fluorescence microscopy. In some embodiments, the biomolecules are low copy-number proteins in cells. In some embodiments, the biomolecules are selected from a bait biomolecule and a prey biomolecule. The bait biomolecule is one that is known or suspected of having an interaction with another biomolecule (prey biomolecule) within or on the selected cell. The prey biomolecule is then complexed with a primary, or primary-secondary antibody complex, wherein one or more of the prey biomolecule, primary antibody, or secondary antibody are fluorescently labeled with a fluorophore. In some embodiments, the imaging can be performed by fluorescence microscopy. The fluorescence microscopy can be selected from TIRF or confocal microscopy. The primary antibody can be added alone, or as a complex with a secondary antibody, to the prey biomolecule-bait biomolecule complex. In some embodiments, the primary antibody is first added to the prey biomolecule-bait biomolecule complex followed by the addition of a secondary antibody (against the primary prey antibody).

The invention provide, inter alia, methods for identifying a biomolecule-biomolecule interaction, the method comprising the steps: (a) contacting a substrate comprising a plurality of micron-sized features with one or a plurality of cell types, wherein a portion or all of the one or plurality of cell types enter a portion or all of the plurality of micron-sized features; (b) presenting a plurality of antibody-coated magnetic beads to said substrate, wherein the antibody-coated magnetic beads comprise an antibody to a bait biomolecule; (c) optionally, applying a magnetic field to said antibody-coated beads; (d) contacting said substrate with a lysis buffer; (e) forming a complex selected from the antibody of the antibody-coated magnetic beads and a bait biomolecule, the bait biomolecule and the prey biomolecule, or all of the antibody of the antibody-coated magnetic beads to the bait biomolecule to the prey biomolecule; (f) presenting an antibody or antibody complex to the prey biomolecule; (g) imaging the antibody or antibody complex to the prey biomolecule by fluorescence microscopy. In some embodiments, the cells can comprise a bait biomolecule and/or a prey biomolecule. In some embodiments, the antibody or antibody complex to the prey biomolecule can be fluorescently labelled. In some embodiments, the antibody complex to the prey biomolecule can comprise a primary antibody to the prey biomolecule, and a secondary antibody to said primary antibody to the prey biomolecule, wherein the secondary antibody can be fluorescently labeled. In some embodiments, the prey biomolecule and bait biomolecule can be independently selected from: proteins, DNA, RNA, mRNA, tRNA, cRNA, antibodies, antibody fragments, ScFv's, peptides, and small molecules.

In some embodiments, the step of (g) imaging the antibody or antibody complex to the prey biomolecule by fluorescence microscopy, can be performed by TIRF or confocal microscopy.

In some embodiments, one prey biomolecule is isolated per nanometer-sized functionalized bead.

EXAMPLES

The work described in these Examples evaluated and demonstrated the positive effect of using the antibody-coated magnetic nanobeads and substrates comprising a plurality of micron-sized features for the single-cell isolation and compositional analysis thereof.

Example 1

General Representative Process of Nanobead-Based Single-Cell Isolation and Analysis for Cell Populations Streptavidin-coated magnetic nanobeads were modified by immobilizing the primary antibody on their surface for capturing the target protein (bait protein) (as described in the examples herein). Cells were lysed and the magnetic nanobeads were added to the lysates and incubated for 30 min, and after the prey protein was captured by the beads, the protein was detected using a specific primary antibody and fluorescently labeled secondary antibodies. The nanobeads were washed thrice to remove nonspecifically bound proteins, transferred to glass slides and covered with coverslips, and imaged using a TIRF microscope. In some embodiments, the bait protein or the prey protein was fluorescently labeled for direct visualization. (FIG. 1)

Example 2

Nanobead-Based SiMPull for Green Fluorescent Protein (GFP) Pull-Down in Cell Populations The nanobead-based SiMPull method was first validated for protein pulldown by pulling down GFP because GFP can be directly visualized without immunostaining, which simplifies the validation, and, more importantly, because GFP can be used in photobleaching experiments to assess the single-molecule state of a fluorescent spot that is pulled down.

Figures 2A, 2B, 2C:
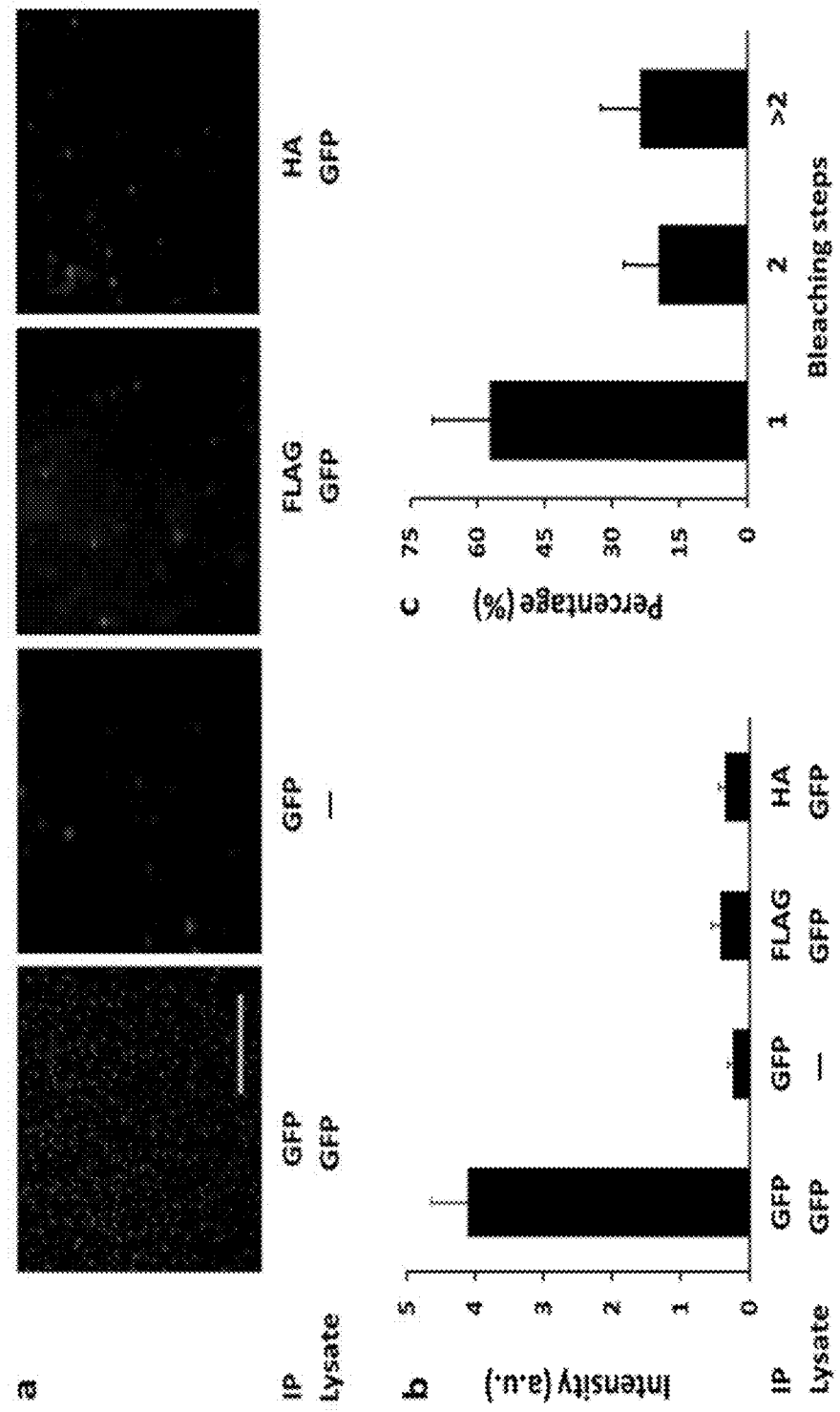
FIGS. 2a-2c show the GFP pull-down using nanobead-based SiMPull.

Ectopic GFP in HEK293T cells was pulled down using magnetic nanobeads (FIG. 2a). By contrast, few GFP molecules were pulled down in a negative-control experiment (FIG. 2a), and the calculated signal-to-noise (SN) ratio of the assay was between about 10-20 (FIG. 2b). This SN ratio is comparable or superior to that of the original SiMPull method of Jain et al. By applying the algorithm previously used by Jain et al., ~95% of fluorescent spots in FIG. 2a displayed Gaussian distribution. These fluorescent spots were subject to photobleaching experiments, and the results suggests that 58% of the spots were single fluorophores (i.e., GFP monomers), 18% two fluorophores, and 22%>2 fluorophores. The spots containing ≥2 fluorophores probably represent ≥2 GFP molecules located within 60-nm (need explain this number, one pixel=60 nm) distance on single nanobeads. 5% of the fluorescent spots that did not show Gaussian distribution were probably tow nanobeads stuck together. These results demonstrated that our bead-based approach enables a protein of interest to be trapped at the single-molecule level with a very high SN ratio.

Example 3

Pull-Down of cAMP-Dependent Protein Kinase a (PKA) Complex in Cell Populations

Figure 3A:
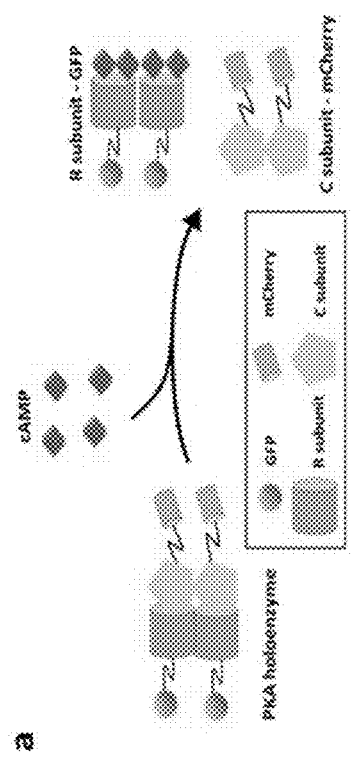
FIGS. 3a-3c show the pull-down method applied to the PKA complex by using nanobead-based methods.

The holoenzyme or complex of PKA, one of the most widely studied protein kinases, exists as a heterotetrametric comprising a regulatory (R) subunit dimer and two catalytic (C) subunits (FIG. 3a); cAMP at physiological levels can bind to the R subunits and release the C subunits from the PKA complex (FIG. 3a). We used the well-characterized interaction between PKA-R and -C subunits to validate the nanobead-based SiMPull assay for studying PPIs.

The expression vectors used in the study were pEGFP-n1 for GFP expression (Addgene Cat. #6085-1), pcDNA3-mouse PKA-C-alpha-mEGFP (Addgene Cat. #45521), and pcDNA3-mouse PKA-RII-alpha-mEGFP (Addgene Cat. #45527). pcDNA3-PKA-C-alpha-mCherry was constructed by replacing the GFP sequence in pcDNA3-PKA-C-alpha-mEGFP with the mCherry sequence.

Figure 3B:
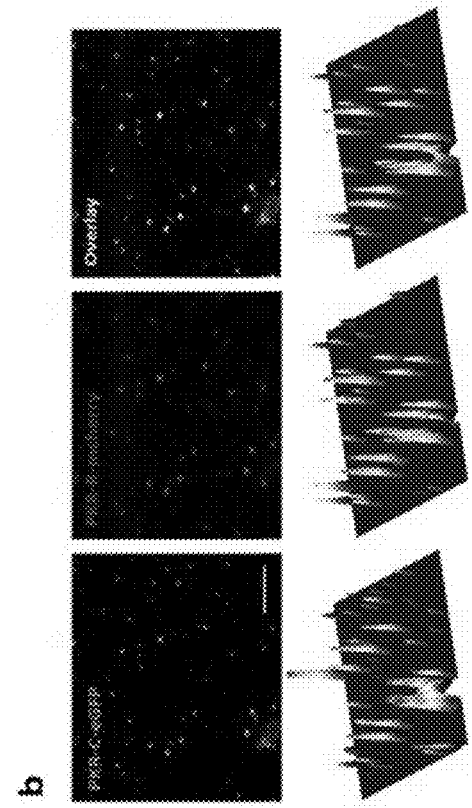

The PKA-C-eGFP and PKA-R-mCherry interaction was examined in HEK293T cells because these fluorescent fusion proteins allow for the direct visualization of PKA-C and -R subunits without immunostaining and facilitate the assessment of pull-down efficiency and specificity (FIG. 3b). When using magnetic nanobeads pre-coated with anti-GFP antibody, both PKA-C-eGFP and PKA-R-mCherry were pulled down. If replacing PKA-R-mCherry with mCherry in these experiments, few mCherry molecules coprecipitated with PKA-C-eGFP (FIG. 3c); this suggests that the interaction between PKA-C-eGFP and PKA-R-mCherry (FIG. 3b) specifically depended on PKA-R. Moreover, the cAMP analog cpt-cAMP disrupted the interaction of PKA-C-eGFP and PKA-R-mCherry (FIG. 10), suggesting that the interaction was physiological.

The majority of the GFP and mCherry signals clearly colocalized (FIG. 3b), although a small fraction did not. This incomplete colocalization of GFP and mCherry could be due to several reasons: (1) only 75% of GFP molecules are properly folded and fluorescent (Waldo, G. S., et al., "Rapid Protein-Folding Assay Using Green Fluorescent Protei,". Nature Biotechnology, 1999; 17(7):691-695); (2) the fluorescence of GFP or mCherry molecules in a complex is unevenly quenched; and (3) unbalanced expression of PKA-C and PKA-R.

Example 4

Schematic and Fabrication of Microwell Array

Figure 4:
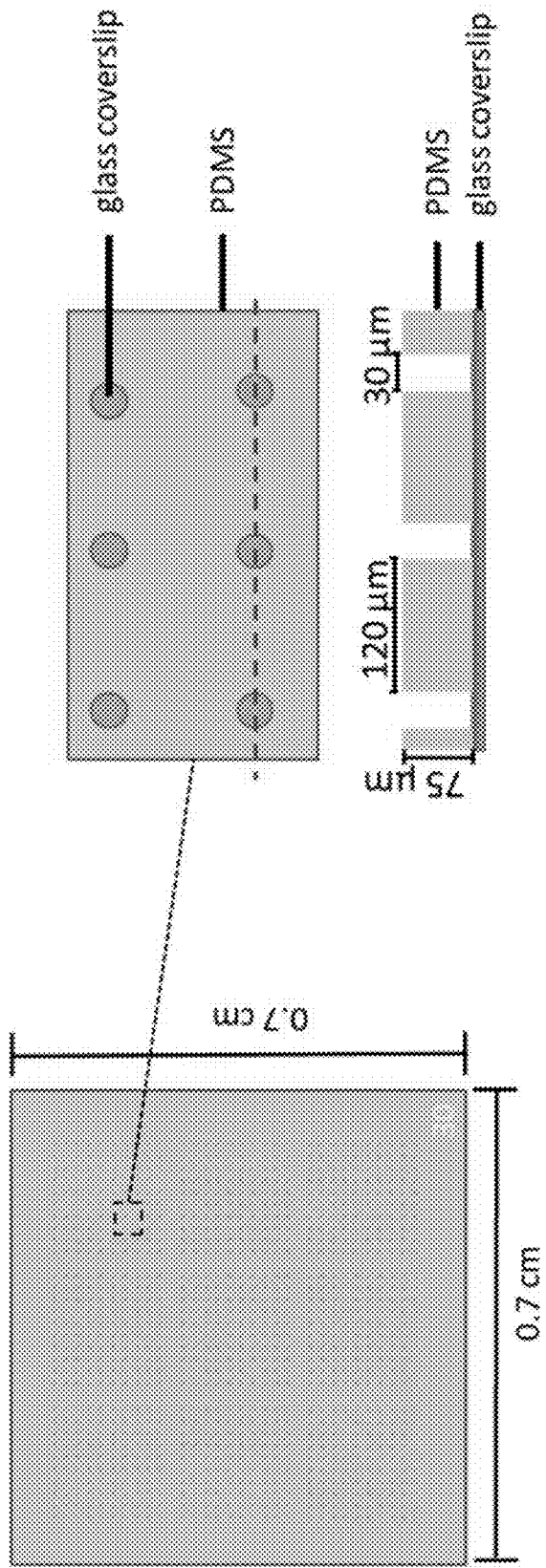
FIG. 4 shows a representative schematic for the single cell microwell array. The schematic top view (left) and cross section (right) of the microwell chip are depicted. The microwell is 30 microns wide and 70 microns deep.
Figures 5A, 5B:
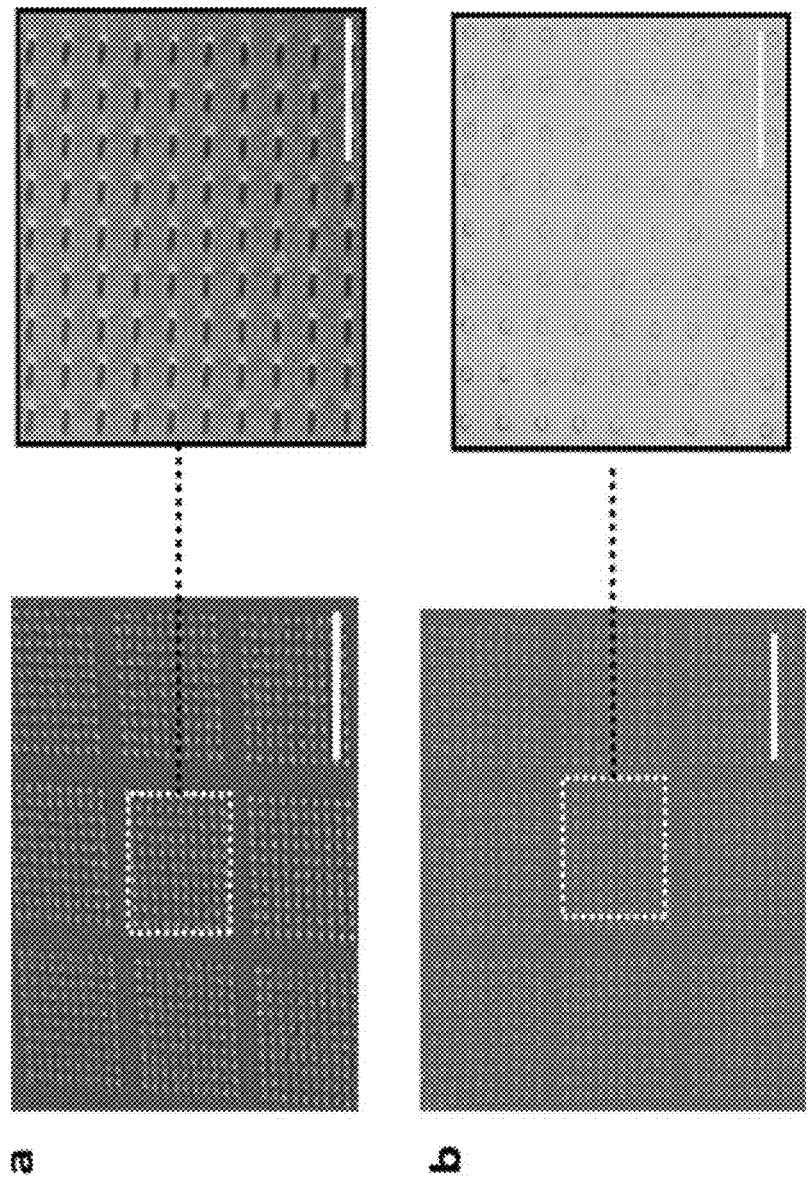
FIGS. 5a & 5b show the fabrication of microwell substrates.

As a representative example of a substrate comprising a plurality of micron-sized features, a microwell array chip was prepared following a previously published procedure with certain modifications (FIG. 4) (Huang, L., et al., "Centrifugation-Assisted Single-Cell Trapping in a Truncated Cone-Shaped Microwell Array Chip for the Real-Time Observation of Cellular Apoptosis," Analytical Chemistry, 2015; 87(24):12169-12176). Depending on the size of the cell of interest, the microwell diameter on each chip was varied (range: 15 microns to 50 microns), and the microwell depth was 70 microns, which was designed to trap cells and to minimize lysate diffusion (FIGS. 4, 5a & 5b).

The fabrication of the cell-trapping microwell arrays was achieved by generating microwell-patterned, porous PDMS membranes on the glass coverslip. Briefly, a silicon mold featuring micropillar patterns was first fabricated by using a Bosch deep-reactive ion etching (DRIE) process. The diameter (ranging from 15 microns to 50 microns) and interspacing (4 times of the diameter of pillars, edge to edge) of the pillars were controlled by using standard photolithographic techniques. The etching depth of the pillars was controlled at 75 microns. The fabricated silicon mold was then diced into chips sized 1.0×1.0 cm$^2$ and silanized with dimethyl-dichlorosilane (Sigma-Aldrich) vapor in a vacuum container overnight, followed by sequential washing with aceton and deionized water and drying by N2 before use. Then, 5 microliters of pre-degassed PDMS pre-polymer (10:1, weight ratio of base to curing agent) was gently poured to the silianized silicon mold and a piece of glass coverslip pretreated with oxygen plasma and washed with acetone (BDH1101), 2-propanol (BDH1133) and DI water in tabletop ultrasonic cleaner (Bransonic) was brought in close contact with the chip, allowing the uniform spreading of the pre-polymer to the whole chip. Subsequently, a 200 g weight was placed over the coverslip to ensure that the microfabricated pillars fully penetrated the pre-polymer layer and touched the glass coverslip. The entire assembly was then placed in a 60° C. oven for 3 h. After removing the weight, the coverslip, together with the microwell-patterned, porous PDMS membrane featuring various sizes, were slowly peeled off from the mold, which formed the cell-trapping device. In some embodiments, the PDMS is a curable polydimethylsiloxane. In some embodiments, the PDMS is SYLGARD 184 Silicone Elastomer Kit (Dow). The PDMS can have a curable component which cross-links the polydimethylsiloxane polymer. In some embodiments, the cross-linker can be Dimethyl, methylhydrogen siloxane copolymer with a platinum catalyst (e.g., hexachloro platinate). In some embodiments, the pre-cure viscosity of the polydimethylsiloxane can be 5100 cP. In some embodiments, the kit viscosity (PDMS with crosslinker) can be 3500 cP. In some embodiments, the PDMS curing time at 100 degrees C. can be 35 minutes or less, or at 150 degrees C. can be 10 minutes or less.

Example 5

Schematic for the Single Cell Pull-Down Assay

Figure 7A:
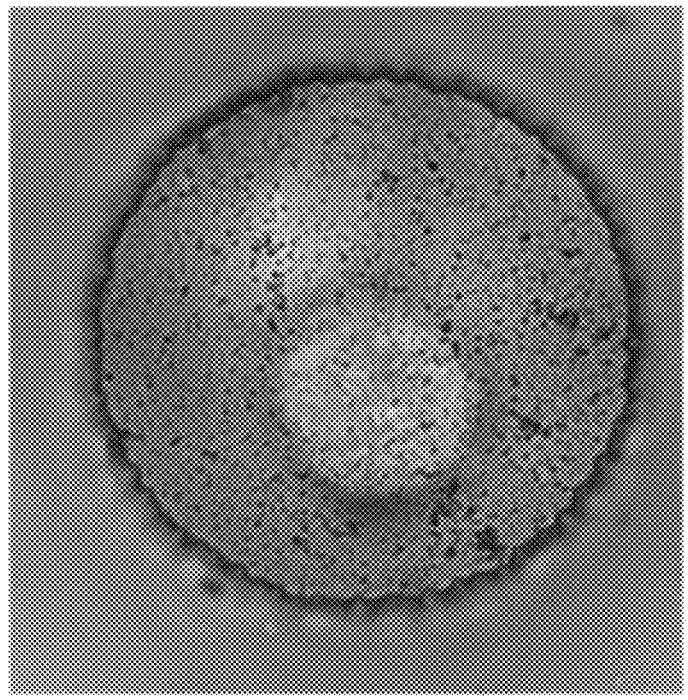
FIGS. 7a & 7b show the application of magnetic beads to a microwell.
Figure 7B:
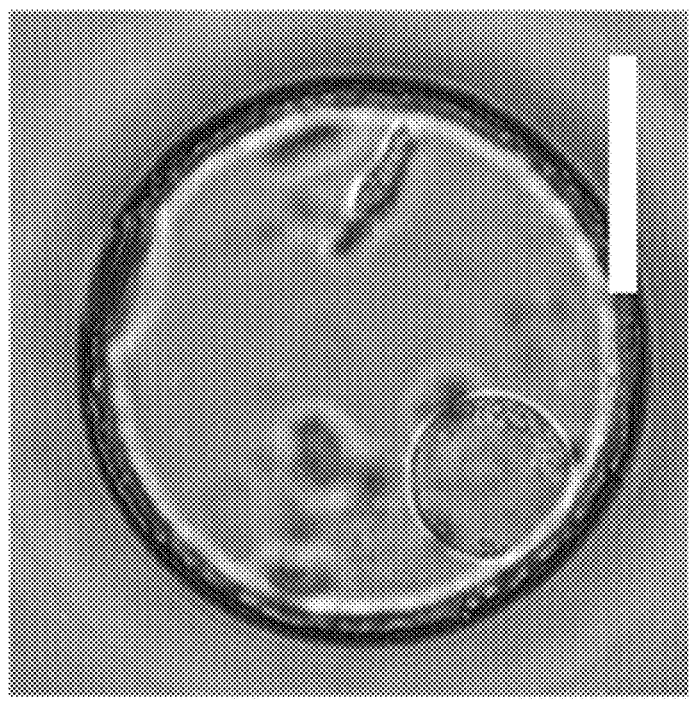
Figures 8A, 8B:
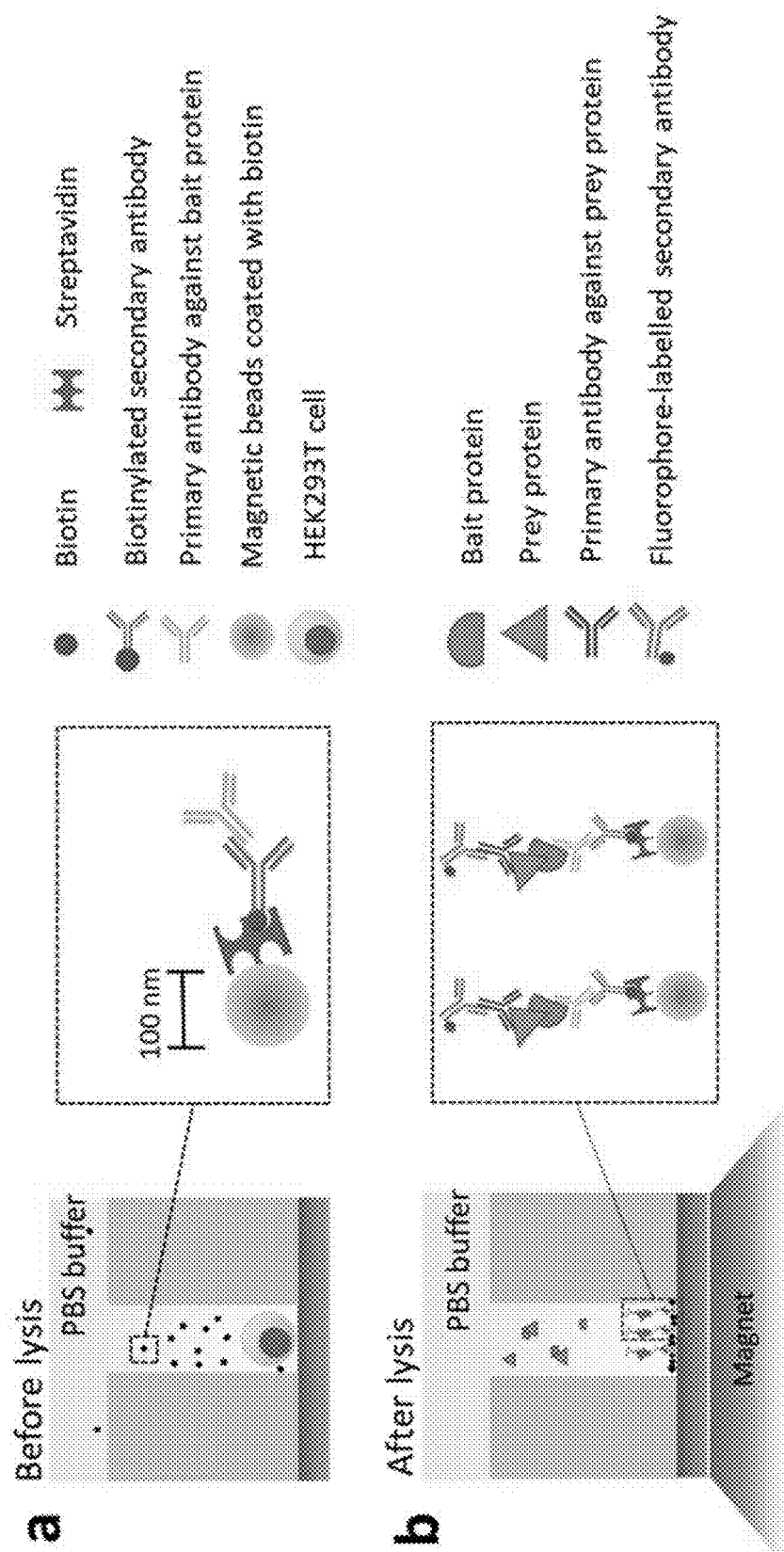
FIGS. 8a & 8b show one representative schematic for the single cell pull-down assay.

First, single cells were trapped in microwells. Next, magnetic nanobeads pre-coated with bait antibodies were applied. In the absence of a magnet, the nanobeads slowly sedimented by gravitational force alone. Application of a magnetic field via an external magnet 3 min pulled the nanobeads down to the microwell bottom (FIGS. 7a & 7b). Subsequently, the lysis buffer was added to the chip to lyse the cells in situ. The bait antibody immobilized on the nanobeads captured the bait and prey proteins in the lysate in the microwell. The magnetic beads remained immobilized at the glass bottom during the entire experiment in the presence of the magnet. The prey proteins, either fluorescently tagged or labeled using immunostaining, were visualized and identified using TIRF or confocal microscopy (FIGS. 8a & 8b).

Fluorescence images from this Example and all the examples were taken using an Olympus IX-73 inverted fluorescence microscope (Olympus) equipped with an oil-immersion objective (NA=1.49, 100×, UAPON, Olympus) as previously described (Alsina et al., 2017) with minor modifications. Images were acquired using an sCMOS camera (Zyla-4.2P-C110, Andor Technology Ltd.). A 488-nm laser (Coherent Inc., USA) was used to excite GFP with an exposure time of 300 ms. Only GFP near the surface of coverslips were excited using an objective total internal reflection illumination. ZT488/561rpc (Chroma) was used as a dichroic mirror, and the emission signals were collected through an ET525/50m (Chroma) emission filter to collect fluorescent signals from GFP. The lasers were focused on the back focusing plane of the objective. A 15× beam expander (Edmond optics, Singapore) and a focus lens were used to illuminate the sample uniformly. Total internal reflection illumination was produced by moving the illumination beam away from the center of the lens. All experiments were performed at room temperature.

The single-cell occupancy (single cell per well) reached approximately 60% (FIG. 6), depending on the density of the cells applied to the chip.

Example 6

Single-Cell GFP Pull-Down

As in FIGS. 9a-9f, the nanobead-based single-cell SiMPull assay was evaluated by pulling down GFP from single cells. After suspension through trypsinization, GFP-expressing HEK293T cells were added to blank microwell chip and subject to SiMPull by magnetic nanobeads, which were applied to the chip surface. GFP was pulled down by magnetic nanobeads coated with anti-GFP antibody through biotinylated 2nd antibody (FIGS. 9a & 9b) but not by nanobeads coated with the 2nd antibody alone (FIGS. 9c & 9d). These results indicate minimal nonspecific GFP binding to the nanobeads, and the SN ratio in these experiments was approximately 12 (FIG. 9e). Moreover, photobleaching revealed that these spots displayed one-step bleaching (FIG. 9f), which indicated the presence of single GFP monomers.

Example 7

Single-Cell Pull-Down of PKA Complex

Figure 3C:
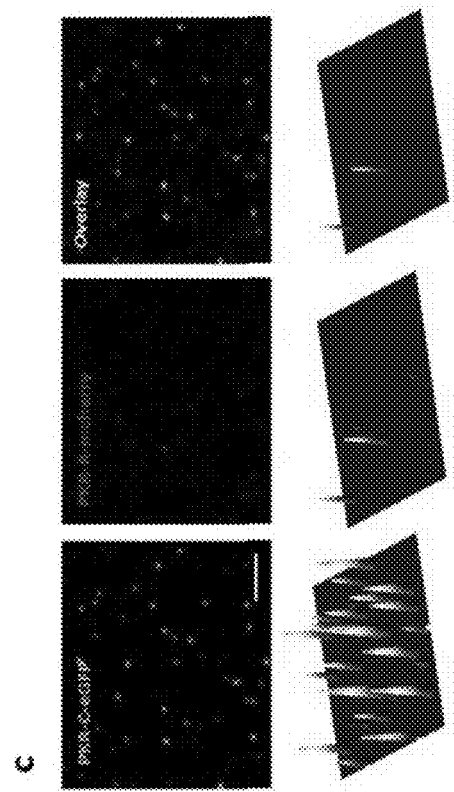
Figures 10A, 10B, 10C, 10D:
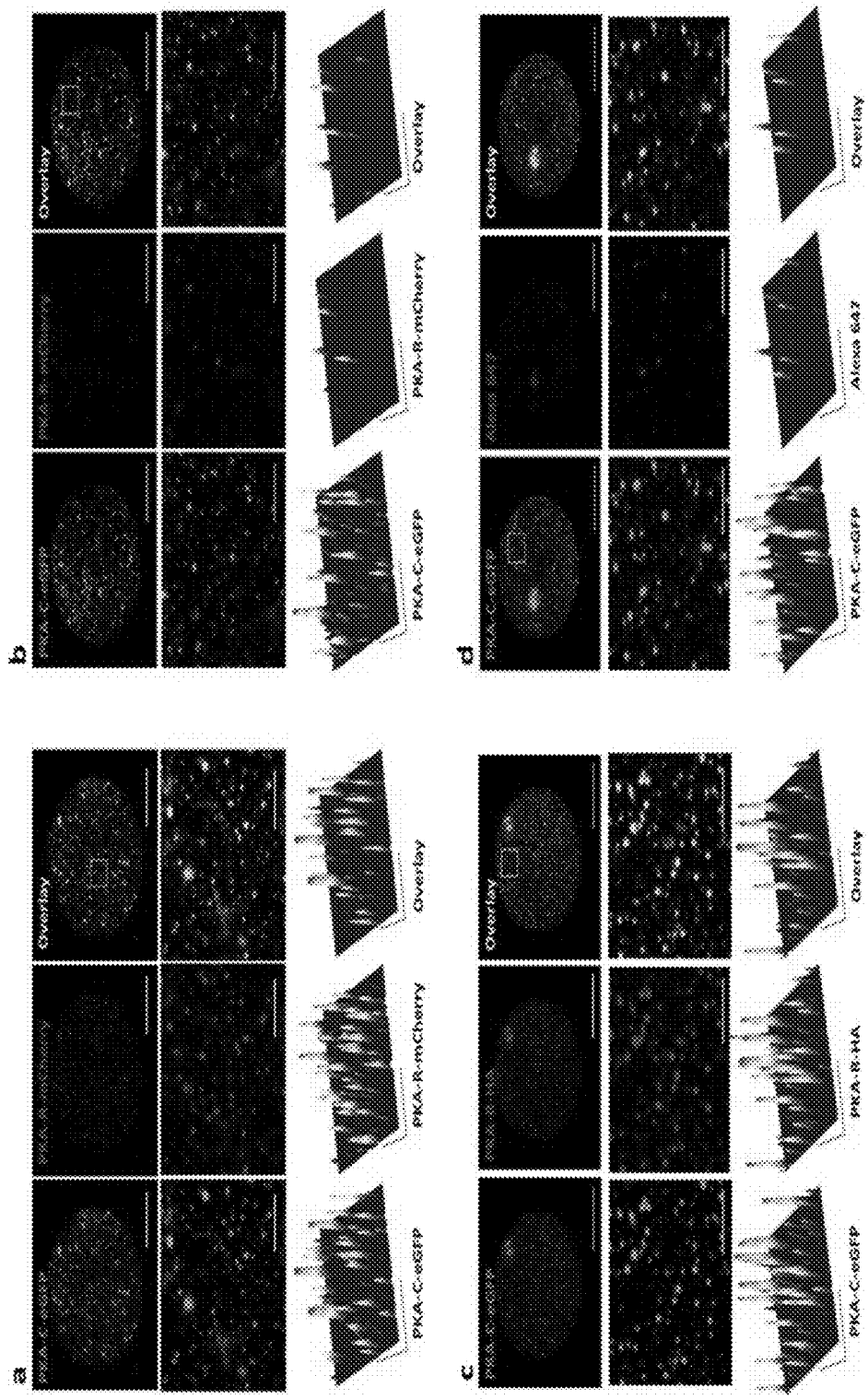
FIGS. 10a-10d show the pull-down of PKA complex in a single cell.

As in FIGS. 3a-3c, the interaction between PKA-R and -C subunits was investigated to validate methods of this disclosure for studying PPIs. The interaction between PKA-C-eGFP and PKA-R-mCherry in single HEK293T cells was investigated (FIG. 10a). When using anti-GFP-coated magnetic nanobeads, both PKA-C-eGFP and PKA-R-mCherry were pulled down, and, notably, few PKA-R-mCherry were pulled down in the presence of the cAMP analog cpt-cAMP (FIG. 10b); this indicates that the PKA-R-mCherry pull-down specifically depended on its physiological interaction with PKA-C-eGFP, rather than on nonspecific binding to the beads or the microwell bottom. Similar to the results shown in FIG. 3b, the majority of the GFP and mCherry signals clearly colocalized, although a small fraction did not (FIG. 10a).

Next, the nanobead-based SiMPull was tested for a more general application: the prey protein (PKA-R) is not fluorescently tagged and requires visualization by immunostaining. A single HEK293T cell coexpressing PKA-C-eGFP and PKA-R-HA was subject to SiMPull using anti-GFP coated nanobeads. After the cell was lysed, a mixture of anti-HA antibody and Alexa-561-conjugated 2nd antibody was added to the chip surface to visualize PKA-R-HA. As shown in FIG. 3e, PKA-R-HA was clearly visible after immunostaining, and ~80% GFP spots colocalized with Alexa-561 spots (FIG. 10c). If PKA-R-H was replaced by PKA-R-GFP in these experiments, few Alexa-561 spots were visible (FIG. 10d), suggesting that the Alexa-561 signal in FIG. 10c was HA-tag specific. Similar reasons for incomplete colocalization of GFP and mCherry spots in FIG. 3b may account for incomplete colocalization of GFP and Alexa spots in FIG. 10c.

The invention described and claimed herein have many attributes and embodiments including, but not limited to, those set forth or described or referenced in this Detailed Disclosure. It is not intended to be all-inclusive and the invention described and claimed herein are not limited to or by the features or embodiments identified in this Detailed Disclosure, which is included for purposes of illustration only and not restriction. A person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, and in embodiments or examples of the invention, any of the terms "comprising", "consisting essentially of", and "consisting of" may be replaced with either of the other two terms in the specification. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of the invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A system comprising a glass substrate comprising a plurality of micron-sized features, a plurality of primary antibodies against a plurality of bait molecules, the plurality of bait molecules, a plurality of target prey biomolecules, and a plurality of primary antibodies against said plurality of target prey biomolecules, wherein the plurality of primary antibodies against the plurality of bait molecules coat a plurality of beads.

2. The system of claim 1, wherein a plurality of secondary antibodies against the primary antibodies against the plurality of bait molecules coat the plurality of beads.

3. The system of claim 1, further comprising one or a plurality of types of cells.

4. The system of claim 3, wherein the cells comprise one or a plurality of a type of target prey biomolecule.

5. The system of claim 3, wherein the plurality of cells are located in the plurality of micron-sized features.

6. The system of claim 3, wherein the plurality of types of cells comprises cells having an average diameter of less than the diameter of the mean average round holes of the wells.

7. The system of claim 6, wherein the plurality of types of cells comprises cells having an average diameter of about 30 microns.

8. The system of claim 3, wherein the plurality of target prey biomolecules comprises molecules which are found in the cell membrane of said cells.

9. The system of claim 3, wherein the plurality of target prey biomolecules comprises molecules which are found in the cytoplasm of said cells.

10. The system of claim 1, wherein the plurality of antibody-coated beads are within the plurality of micron-sized features.

11. The system of claim 1, further comprising a cell lysis buffer.

12. The system of claim 11, wherein the cell lysis buffer comprises a non-denaturing detergent.

13. The system of claim 1, wherein the plurality of antibody-coated beads comprises a secondary antibody to the plurality of primary antibodies to a bait biomolecule.

14. The system of claim 1, wherein the plurality of micron-sized features comprises a series of wells having round holes each of which having a mean average diameter between about 15 microns to about 45 microns, a mean average distance between a center of each hole ranging from about 100 microns to about 5000 microns, and a mean average depth of each hole of about 25 microns to about 150 microns.

15. The system of claim 14, wherein the mean average diameter of the series of wells is about 30 microns.

16. The system of claim 14, wherein the mean average distance between the center of each hole is about 150 microns.

17. The system of claim 14, wherein the mean average depth of each hole is about 75 microns.

18. The system of claim 1, wherein the plurality of antibody-coated beads comprise magnetic beads.

19. The system of claim 18, wherein the magnetic bead comprises an iron oxide core.

20. The system of claim 18, further comprising a magnet.

21. The system of claim 1, wherein the plurality of micron-sized features is directly etched into the glass substrate.

22. The system of claim 1, wherein the plurality of micron-sized features is formed from polydimethylsiloxane (PDMS).

23. The system of claim 22, wherein the PDMS is cured PDMS.

24. The system of claim 1, wherein the glass substrate is a glass coverslip having a thickness of 0.085 mm to 0.64 mm.

25. The system of claim 24, wherein the glass substrate is configured to be measureable by TIRF (total internal reflectance spectroscopy).

26. The system of claim 1, wherein the bait molecules and the plurality of target prey biomolecules are independently selected from the group consisting of proteins, DNA, RNA, mRNA, tRNA, cRNA, antibodies, antibody fragments, ScFv's, and peptides.

27. The system of claim 26, wherein the DNA or RNA is modified with biotin.

\* \* \* \* \*